US008613726B2

(12) United States Patent
Causey, III et al.

(10) Patent No.: US 8,613,726 B2
(45) Date of Patent: Dec. 24, 2013

(54) CONTROL TABS FOR INFUSION DEVICES AND METHODS OF USING THE SAME

(75) Inventors: James D. Causey, III, Simi Valley, CA (US); William H. Stutz, Jr., Eagle Rock, CA (US); Clyde K. Nason, Valencia, CA (US); Sheldon B. Moberg, Granada Hills, CA (US); Jay Yonemoto, Diamond Bar, CA (US); Richard E. Purvis, Pasadena, CA (US); Cary Talbot, Santa Clarita, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

(21) Appl. No.: 12/689,887

(22) Filed: Jan. 19, 2010

(65) Prior Publication Data

US 2010/0160861 A1 Jun. 24, 2010

Related U.S. Application Data

(60) Division of application No. 11/593,210, filed on Nov. 6, 2006, now abandoned, which is a division of application No. 09/813,660, filed on Mar. 21, 2001, which is a continuation of application No. 09/672,244, filed on Sep. 28, 2000, now abandoned, which is a continuation of application No. 09/533,578, filed on Mar. 23, 2000, now Pat. No. 6,752,787.

(51) Int. Cl.
*A61M 37/00* (2006.01)

(52) U.S. Cl.
USPC ........... 604/131; 604/132; 604/151; 604/152; 604/153; 604/155; 604/156; 604/232; 604/246; 604/253; 604/264; 604/140

(58) Field of Classification Search
USPC ......... 604/131, 132, 151–156, 232, 246, 253, 604/264, 140
See application file for complete search history.

(56) References Cited

U.S. PATENT DOCUMENTS

| 3,498,228 A | 3/1970 | Blumle et al. |
| 3,886,938 A | 6/1975 | Szabo et al. |

(Continued)

FOREIGN PATENT DOCUMENTS

| CH | 665955 | 6/1988 | |
| DE | EP 1079776 | * 5/1999 | .............. A61F 9/007 |

(Continued)

OTHER PUBLICATIONS

International Search Report for International Application No. PCT/US01/09139.

(Continued)

*Primary Examiner* — Nicholas Lucchesi
*Assistant Examiner* — Scott Medway
(74) *Attorney, Agent, or Firm* — Medtronic MiniMed, Inc.

(57) ABSTRACT

An external infusion device that infuses a fluid into an individual's body includes a housing, a reservoir, a drive system, a power supply, electrical elements, and a tab. The reservoir contains the fluid, and the drive system forces the fluid from the reservoir. The electrical elements control the power to the drive system to regulate the rate that fluid is forced from the reservoir. The tab mates with the housing, and contains at least one electrical element. The tab is removable, and may be replaced with a different tab. The different tab may change the rate fluid is forced from the reservoir. A tab may be removed from one external infusion device and installed in a different external infusion device. The tab may be limited to use in a predetermined number of external infusion devices and may include a power supply.

20 Claims, 20 Drawing Sheets

(56) References Cited

U.S. PATENT DOCUMENTS

| | | | |
|---|---|---|---|
| 3,895,631 A | 7/1975 | Buckles et al. | |
| 4,210,138 A | 7/1980 | Jess et al. | |
| 4,231,366 A | 11/1980 | Schael | |
| 4,269,185 A | 5/1981 | Whitney et al. | |
| 4,270,532 A | 6/1981 | Franetzki et al. | |
| 4,373,527 A | 2/1983 | Fischell | |
| 4,397,639 A * | 8/1983 | Eschweiler et al. | 604/153 |
| 4,498,843 A | 2/1985 | Schneider et al. | |
| 4,529,401 A | 7/1985 | Leslie et al. | |
| 4,543,955 A | 10/1985 | Schroeppel | |
| 4,596,575 A * | 6/1986 | Rosenberg et al. | 604/891.1 |
| 4,636,144 A * | 1/1987 | Abe et al. | 417/63 |
| 4,657,490 A * | 4/1987 | Abbott | 417/478 |
| 4,685,902 A * | 8/1987 | Edwards et al. | 604/153 |
| 4,718,896 A * | 1/1988 | Arndt et al. | 604/253 |
| 4,731,051 A * | 3/1988 | Fischell | 604/67 |
| 4,734,092 A * | 3/1988 | Millerd | 604/67 |
| 4,781,548 A * | 11/1988 | Alderson et al. | 417/474 |
| 4,877,745 A * | 10/1989 | Hayes et al. | 436/166 |
| 4,886,499 A * | 12/1989 | Cirelli et al. | 604/131 |
| 4,908,017 A * | 3/1990 | Howson et al. | 604/67 |
| 5,131,816 A * | 7/1992 | Brown et al. | 417/2 |
| 5,135,479 A * | 8/1992 | Sibalis et al. | 604/20 |
| 5,167,617 A * | 12/1992 | Sibalis | 604/20 |
| 5,279,558 A * | 1/1994 | Kriesel | 604/85 |
| 5,368,562 A * | 11/1994 | Blomquist et al. | 604/65 |
| 5,373,852 A | 12/1994 | Harrison et al. | |
| 5,378,231 A * | 1/1995 | Johnson et al. | 604/67 |
| 5,429,602 A | 7/1995 | Hauser | |
| 5,474,527 A * | 12/1995 | Bettinger | 604/19 |
| 5,485,408 A | 1/1996 | Blomquist | |
| 5,487,386 A * | 1/1996 | Wakabayashi et al. | 600/437 |
| 5,496,363 A * | 3/1996 | Burgio et al. | 607/152 |
| 5,527,288 A * | 6/1996 | Gross et al. | 604/140 |
| 5,558,639 A * | 9/1996 | Gangemi et al. | 604/67 |
| 5,582,591 A * | 12/1996 | Cheikh | 604/500 |
| 5,582,593 A * | 12/1996 | Hultman | 604/65 |
| 5,584,811 A * | 12/1996 | Ross et al. | 604/141 |
| 5,658,250 A | 8/1997 | Blomquist et al. | |
| 5,681,285 A | 10/1997 | Ford et al. | |
| 5,693,018 A * | 12/1997 | Kriesel et al. | 604/132 |
| 5,697,896 A * | 12/1997 | McNichols et al. | 604/20 |
| 5,722,397 A * | 3/1998 | Eppstein | 600/345 |
| 5,733,313 A * | 3/1998 | Barreras et al. | 607/33 |
| 5,741,313 A | 4/1998 | Davis et al. | |
| 5,744,793 A | 4/1998 | Skell et al. | |
| 5,755,692 A | 5/1998 | Manicom | |
| 5,788,669 A | 8/1998 | Peterson | |
| 5,797,519 A | 8/1998 | Schroeder et al. | |
| 5,830,175 A * | 11/1998 | Flower | 604/20 |
| 5,860,957 A * | 1/1999 | Jacobsen et al. | 604/156 |
| 5,871,125 A * | 2/1999 | Gross | 222/207 |
| 5,873,850 A * | 2/1999 | Flower et al. | 604/20 |
| 5,876,368 A * | 3/1999 | Flower | 604/20 |
| 5,879,322 A * | 3/1999 | Lattin et al. | 604/20 |
| 5,895,371 A | 4/1999 | Levitas et al. | |
| 5,957,895 A * | 9/1999 | Sage et al. | 604/181 |
| 5,960,085 A | 9/1999 | de la Huerga | |
| 5,971,963 A * | 10/1999 | Choi | 604/177 |
| 5,984,894 A | 11/1999 | Poulsen et al. | |
| 5,997,501 A * | 12/1999 | Gross et al. | 604/65 |
| 6,026,325 A | 2/2000 | Weinberg et al. | |
| 6,051,887 A | 4/2000 | Hubbard | |
| RE36,871 E | 9/2000 | Epstein et al. | |
| 6,126,637 A * | 10/2000 | Kriesel et al. | 604/132 |
| 6,142,343 A | 11/2000 | Wade et al. | |
| 6,157,858 A * | 12/2000 | Gross et al. | 604/20 |
| 6,167,302 A * | 12/2000 | Millot | 604/20 |
| 6,349,232 B1 * | 2/2002 | Gordon | 604/20 |
| 6,375,638 B2 | 4/2002 | Nason et al. | |
| 6,377,848 B1 * | 4/2002 | Garde et al. | 604/20 |
| 6,423,035 B1 | 7/2002 | Das et al. | |
| 6,436,078 B1 * | 8/2002 | Svedman | 604/313 |
| 6,445,955 B1 * | 9/2002 | Michelson et al. | 607/46 |
| 6,468,247 B1 * | 10/2002 | Zamoyski | 604/131 |
| 6,752,787 B1 | 6/2004 | Causey, III et al. | |
| 6,997,906 B2 * | 2/2006 | Langley et al. | 604/151 |
| 7,654,127 B2 * | 2/2010 | Krulevitch et al. | 73/1.16 |
| 7,678,102 B1 * | 3/2010 | Heaton | 604/543 |
| 7,708,717 B2 * | 5/2010 | Estes et al. | 604/151 |
| 7,729,733 B2 * | 6/2010 | Al-Ali et al. | 600/310 |
| 7,914,480 B2 * | 3/2011 | Cleary et al. | 604/46 |
| 7,963,945 B2 * | 6/2011 | Miller et al. | 604/131 |
| 8,029,459 B2 * | 10/2011 | Rush et al. | 604/65 |
| 8,175,673 B2 * | 5/2012 | Say et al. | 600/345 |
| 2011/0208155 A1 * | 8/2011 | Palerm et al. | 604/503 |

FOREIGN PATENT DOCUMENTS

| | | | |
|---|---|---|---|
| EP | 0497041 | 8/1992 | |
| EP | 0499903 | 8/1992 | |
| EP | 0575256 | 12/1993 | |
| JP | 5103833 | 4/1993 | |
| WO | 9403222 | 2/1994 | |
| WO | 9407186 | 3/1994 | |
| WO | 9407553 | 4/1994 | |
| WO | 9425089 | 11/1994 | |
| WO | 9524233 | 9/1995 | |
| WO | 9614893 | 5/1996 | |
| WO | WO97/38750 | * 10/1997 | A61N 1/30 |

OTHER PUBLICATIONS

Japanese Patent Office Decision of Final Rejection for Patent Application Serial No. 2001-501284, Mailing Date Aug. 10, 2004 (translation included).

Excerpt from Japanese Utility Model Laid-Open Publication No. Hei 4-83251, dated Jul. 20, 1992.

Database WPI, Section Ch, Week 199843, Derwent Publication Ltd., London, GB; AN 1998-505404, XP002144981 (Patent Solutions Inc) abstract, & US 5 803 712 A (Davis Davis L et al) Sep. 8, 1998.

* cited by examiner

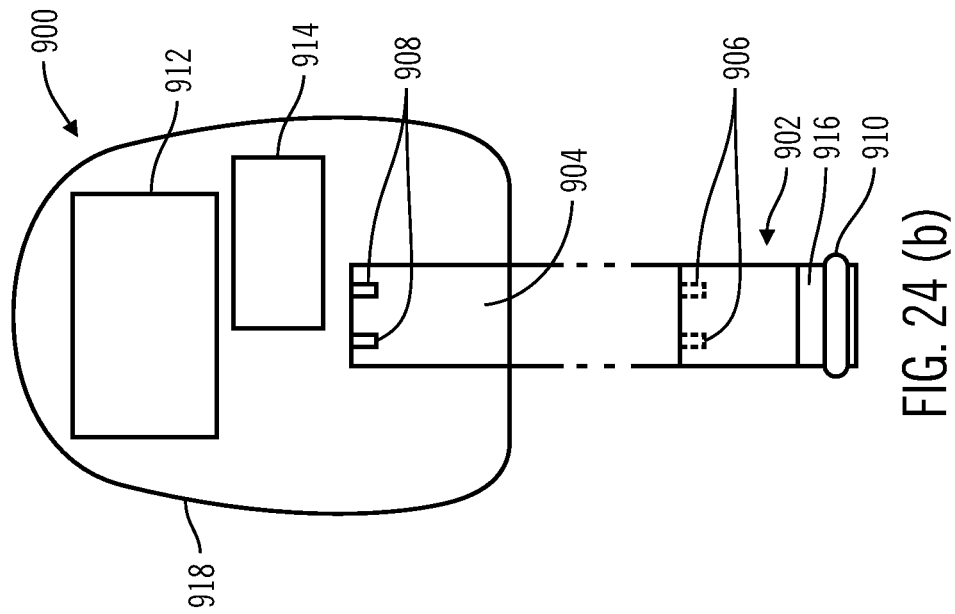
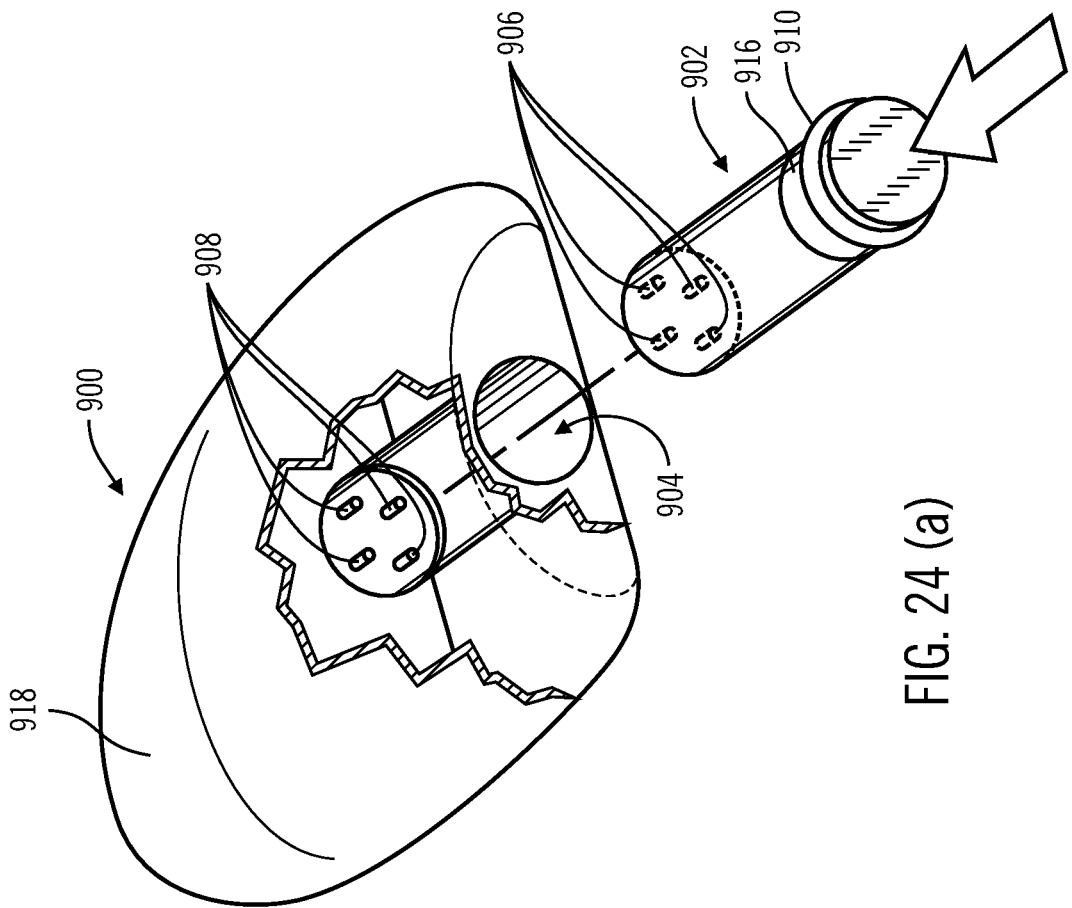

CONTROL TABS FOR INFUSION DEVICES AND METHODS OF USING THE SAME

RELATED APPLICATIONS

This application is a divisional of U.S. patent application Ser. No. 11/593,210, filed on Nov. 6, 2006, now abandoned, and entitled "Control Tabs for Infusion Devices and Methods of Using the Same," which is a divisional of U.S. patent application Ser. No. 09/813,660, filed on Mar. 21, 2001, and entitled "Control Tabs for Infusion Devices and Methods of Using the Same," which is a continuation of U.S. patent application Ser. No. 09/672,244, filed on Sep. 28, 2000, now abandoned, and entitled "Cost-Sensitive Application Infusion Device," which is a continuation of U.S. patent application Ser. No. 09/533,578, filed on Mar. 23, 2000, and entitled "Cost-Sensitive Application Infusion Device," now U.S. Pat. No. 6,752,787, all of which are specifically incorporated by reference herein.

FIELD OF THE INVENTION

This invention relates to external infusion devices and, in particular embodiments to external infusion devices that control the rate that a fluid is infused into an individual's body.

BACKGROUND OF THE INVENTION

Portable personal infusion devices and systems are relatively well-known in the medical arts, for use in delivering or dispensing a prescribed medication to a patient. Many pharmaceutical agents are delivered into the subcutaneous tissue and the most common is insulin. Currently, more than 70,000 patients in the U.S. and 30,000 more patients worldwide use continuous subcutaneous infusion of insulin (CSII) for the treatment of diabetes mellitus. However, other medications that are infused include HIV drugs, drugs to treat pulmonary hypertension, iron chelation drugs, pain medications, and anti-cancer treatments.

Traditionally, low cost infusion devices have used an elastomeric diaphragm, sponge rubber, balloon or gas generator to expel fluid to be infused into a patient over a period of time at a single, relatively constant rate. A drawback to these devices is that they are only filled with fluid once. When the infusion of fluid is complete, the infusion device is disposed of. Thus, the infusion device must be made at an extremely low cost. Another drawback is that the low cost may not allow for the high quality needed to have sufficient flow rate control accuracy for the delivery of dosage sensitive drugs.

To obviate these drawbacks, infusion devices have been designed with more accurate dosage control, but at a significantly higher cost. To compensate for the relatively high cost, the more accurate infusion devices are designed to be refilled and reused.

In one form, refillable infusion devices comprise a relatively compact housing adapted to receive a syringe or reservoir carrying a prescribed medication for administration to the patient through infusion tubing and an associated catheter or infusion set. Such infusion devices are utilized to administer insulin and other medications, with exemplary infusion device constructions being shown and described in U.S. Pat. Nos. 4,562,751; 4,678,408; 4,685,903; 5,080,653 and 5,097,122, which are incorporated by reference herein.

While the sophisticated electronics and robust mechanics of the more expensive refillable infusion devices provide a more reliable and accurate infusion device, the cost of manufacturing may make the refillable infusion device too expensive for some users or medications. On the other hand, the low cost, one-time-use, constant flow rate infusion devices may not have sufficient flow rate accuracy or the adjustments needed to control the dosage for some users.

SUMMARY OF THE DISCLOSURE

According to an embodiment of the invention, a reusable external infusion device with a predetermined usage life for infusing a fluid into a body includes a replaceable reservoir, a power supply, a drive system, an electronics system, and a housing. The housing contains the reservoir, power supply, drive system, and electronics system. The replaceable reservoir contains the fluid before infusing and has a usage life substantially shorter than the predetermined usage life of the infusion device. The power supply provides power to the drive system and the electronics system to force fluid from the reservoir. The electronics system regulates the power from the power supply to control the drive system.

In particular embodiments of the present invention, the infusion device includes a control system operatively coupled to the electronics system that adjusts one or more control parameters. In more particular embodiments, the control system is a supplemental device. In additional embodiments, the supplemental device establishes two way communication with the electronics system. In particular embodiments, the supplemental device has a display.

In preferred embodiments, after the infusion device's predetermined usage life has expired, the infusion device may be refurbished at least once to function for another predetermined usage life. In particular embodiments, when the predetermined usage life for the infusion device expires, the infusion device ceases to infuse fluid. In further particular embodiments, the predetermined usage life for the infusion device is programmed into a software program as a number of times that the replaceable reservoir is replaced in the infusion device.

In preferred embodiments, the drive mechanism of the infusion device contains a DC motor in the drive system. In alternative embodiments, the drive mechanism of the infusion device contains a stepper motor, solenoid motor, a shape memory alloy driven motor, or the like.

According to another embodiment of the present invention, a reusable external infusion device is for infusing a fluid into an individual. In preferred embodiments, the infusion device includes a housing and a replaceable fluid containing reservoir that is inserted into the housing. In preferred embodiments, the housing contains only one electronics module to control the infusion device. In particular embodiments, the electronics module contained within the housing is produced using chip-on-board construction. In other particular embodiments, the electronics module contained within the housing is produced using ball grid array construction. In further embodiments, the electronics module a flex circuit to control the infusion device. In preferred embodiments, the housing contains a detection device that detects the presence or absence of the replaceable reservoir. In further preferred embodiments, the reusable external infusion device further includes a drive mechanism coupled to an electronics system and the housing includes a button coupled to the electronics system that an individual may push to cause the drive mechanism to deliver a bolus of fluid into the individual.

In additional preferred embodiments, the housing and internal contents are assembled together without screws. In more preferred embodiments, the housing includes at least one feature that is fused using ultrasonic vibrations. In other preferred embodiments, the housing includes a drive mechanism that contains at least one non-metallic gear.

In preferred embodiments, the housing includes a slidable key that provides access to remove and/or replace the replaceable reservoir inside the housing. In particular embodiments, the housing accepts a key that includes a communication device for communicating with a supplemental device. In alternative embodiments, the housing accepts a tab that includes a communication device for communicating with a supplemental device. In further alternative embodiments, the housing accepts a tab/key that includes a communication device for communicating with a supplemental device.

In further preferred embodiments, the housing includes an opening to insert a removable tab that includes a programmable chip that contains at least one control parameter to control the infusion device. In further embodiments, the housing includes an opening to insert a tab that includes at least one electrical terminal that establishes electrical contact between at least one set of electrical terminals inside the housing. In particular embodiments, the housing is adapted to receive at least one of at least two different tabs that are insertable into the housing, and the at least two different tabs each have different electrical terminal configurations that establish electrical contact between different electrical terminals inside the housing, and connects different electrical terminals to cause the external infusion device to dispense fluid at different rates. In still further embodiments, the housing is adapted to receive at least one tab with an optically readable pattern, and the housing includes an optical reader to read the optically readable pattern on the at least one tab to control at least one control parameter of the reusable external infusion device. In alternative embodiments, the housing is adapted to receive at least one tab that includes magnetically stored information, and the housing includes a magnetic reader to read the magnetically stored information from the at least one tab to control at least one control parameter of the reusable external infusion device.

In preferred embodiments, the reusable external infusion device includes at least one lithium magnesium oxide ($LiMnO_2$) battery. In particular embodiments, the reusable external infusion device includes a battery that lasts at least 10 weeks, measured while the reusable external infusion device dispenses up to 40 milliliters of fluid per day and while the alarms draw substantially no power from at least one battery.

In additional particular embodiments, an alarm is activated when the reusable external infusion device needs to be refurbished. In preferred embodiments, the reusable external infusion device has a predetermined usage life and when the predetermined usage life has expired, the reusable external infusion device may be refurbished at least once to function for another predetermined usage life. In particular embodiments, the reusable external infusion device has a predetermined usage life and when the predetermined usage life expires, the reusable external infusion device ceases to infuse fluid.

In further particular embodiments, the reusable external infusion device has a predetermined usage life and the predetermined usage life for the reusable external infusion device is programmed into a software program as a number of times that the replaceable reservoir is replaced in the housing, as a number of days that the reusable external infusion device is in use, as the number of times the battery is replaced in the reusable external infusion device, and/or as the number of times that a key is removed from the reusable external infusion device. In other embodiments, the reusable external infusion device has a predetermined usage life and the predetermined usage life for the reusable external infusion device is expired when the amount of electrical power consumed to empty a reservoir exceeds a predetermined amount programmed into a software program.

According to an embodiment of the invention, an external infusion device for infusing a fluid into a body includes a housing, a reservoir, a drive system, at least one power supply, one or more electrical elements, and a tab. The housing contains the reservoir and the drive system. The reservoir contains the fluid, and the drive system forces the fluid from the reservoir. The drive system is powered by the at least one power supply. The one or more electrical elements are coupled to the power supply and the drive system to regulate the rate that the drive system forces fluid from the reservoir. The tab mates with the housing, and contains at least one of the one or more electrical elements. In preferred embodiments, the tab is removable, and in particular embodiments is replaceable with a different tab. In some embodiments, the different tab changes the rate that the drive system forces fluid from the reservoir. In particular embodiments, the tab may be removed from one external infusion device and mated with a different external infusion device to affect the operation of the different external infusion device. In other particular embodiments, the tab may only be used in a predetermined number of external infusion devices. In further embodiments, the tab includes at least one of the at least one power supply.

In preferred embodiments, the tab is insertable into an opening in the housing, and may include a seal to improve resistance to water or contaminants entering the housing. Alternatively, the tab is attachable to the exterior of the housing. In alternative embodiments, the housing includes a seal that is in contact with the tab to improve resistance to water or contaminants entering the housing.

In alternative embodiments, the tab is disposable, and in some embodiments, the tab, once it is installed, is not removable from the housing. In other embodiments, the reservoir of the external infusion device can only be filled once.

In preferred embodiments, the tab affects whether a medicament filling apparatus can mate with the infusion device. In alternative embodiments, the tab affects whether or not a fluid path between a medicament filling apparatus and the reservoir is open.

In particular embodiments, the tab includes all of the one or more electrical elements. In other embodiments, the tab includes at least a portion of the drive system. In still other embodiments, the tab includes the drive system. In yet another embodiment, the tab includes one or more components that are sensitive to sterilization treatments. And in still another embodiment, the tab includes one or more components that are reusable.

In particular embodiments, the tab includes one or more indicators. In preferred embodiments, the one or more indicators indicate that the drive system is powered. In other embodiments, the one or more indicators indicate that fluid delivery is in process. And in still other embodiments, the one or more indicators indicate a power supply status.

According to an embodiment of the invention, a tab for an external infusion device having a housing containing a reservoir for fluid to be infused into a body and a drive system to force the fluid from the reservoir powered by at least one power supply and controlled by one or more electrical elements includes a support structure and at least one of the one or more electrical elements. The support structure mates with the housing of the external infusion device, and the at least one of the one or more electrical elements is attached to the support structure. In preferred embodiments, the tab affects the rate that the fluid is infused into the body. Furthermore, the tab is insertable into an opening in the housing, and includes a seal to improve resistance to water or contaminants entering the housing. In alternative embodiments, the tab is attachable to the exterior of the housing. In other alternative embodiments, once the tab is installed, it contacts a seal on the housing that improves resistance to water or contaminants entering the housing.

In preferred embodiments, the tab is removable, and in some embodiments, the tab may be removed form one external infusion device and mated with a different external infusion device to affect at least one control parameter of the different external infusion device. In particular embodiments, the tab may only be used in a predetermined number of external infusion devices.

In alternative embodiments, the tab is disposable and in some embodiments, after it is installed, the tab is not removable from the housing. In further alternative embodiments, the tab can only be used once. In other alternative embodiments, the tab includes at least one of the at least one power supply. In further embodiments, the tab includes at least a portion of the drive system.

In some embodiments, the tab affects whether a medicament filling apparatus can mate with the infusion device. In other embodiments, the tab affects whether or not a fluid path between a medicament filling apparatus and the reservoir is open.

Other features and advantages of the invention will become apparent from the following detailed description, taken in conjunction with the accompanying drawings, which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 19($b$) is a perspective view of a communication key with a connector and wire attached in accordance with an embodiment of the present invention.

FIG. 23($b$) is a top plan view showing a rough layout of internal components of an infusion device, which has a tab in accordance with an embodiment of the present invention.

FIG. 24($a$) is a partial cutout perspective view of an infusion device with a tab containing at least one battery in accordance with an embodiment of the present invention.

FIG. 24($b$) is a top plan view showing a rough layout of internal components of an infusion device, which has a tab containing at least one battery in accordance with an embodiment of the present invention.

FIG. 25($b$) is a top plan view showing a rough layout of internal components of an infusion device, which has a tab containing at least one battery, at least one electrical component, and a drive system in accordance with an embodiment of the present invention.

DETAILED DESCRIPTION OF THE PREFERRED EMBODIMENTS

Figure 1:
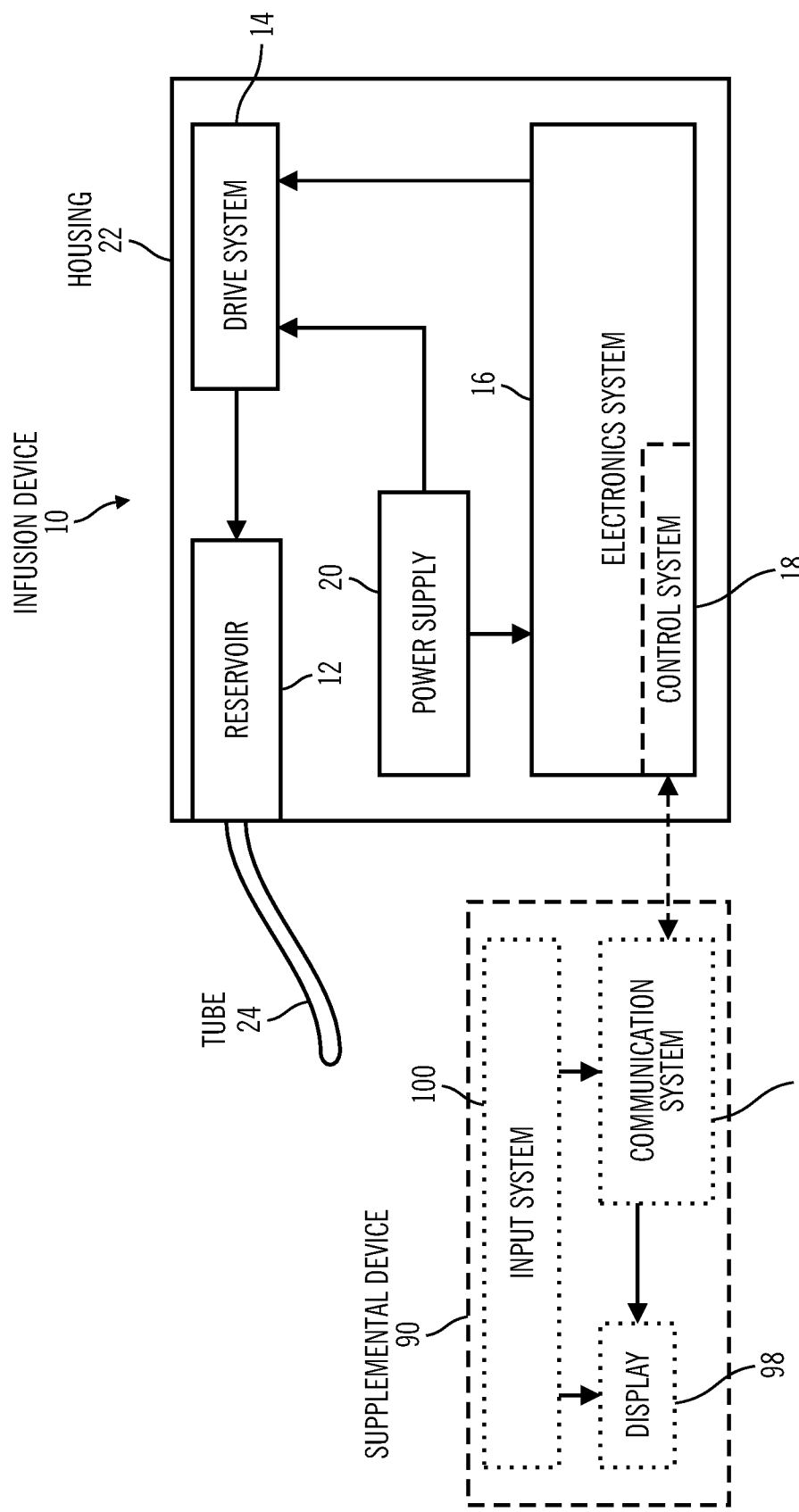
FIG. 1 is a block diagram, illustrating an infusion device and a supplemental device according to an embodiment of the present invention.

As shown in the drawings for purposes of illustration, the invention is embodied in a reusable external infusion device for infusing a fluid into an individual's body and methods of manufacturing the same. The infusion device controls the rate that fluid flows from a reservoir inside a housing, through an external tube, and into the individual's body. In preferred embodiments, the infused fluid is insulin. In alternative embodiments, many other fluids may be administered through infusion such as, but not limited to, HIV drugs, drugs to treat pulmonary hypertension, iron chelation drugs, pain medications, anti-cancer treatments, vitamins, hormones, or the like.

Figure 2:
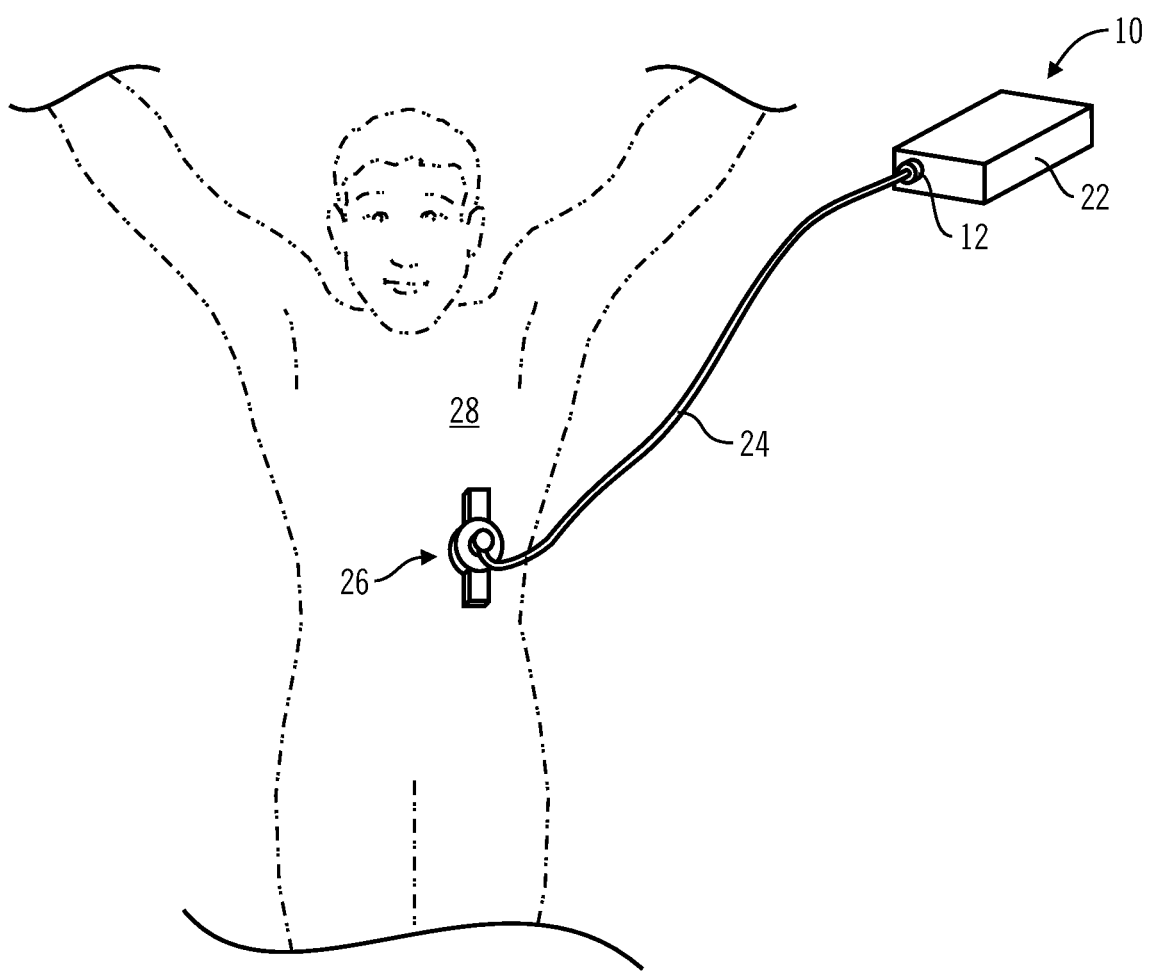
FIG. 2 is a perspective view of an infusion device connected to a tube, an infusion set and an individual's body according to an embodiment of the present invention.
Figure 3:
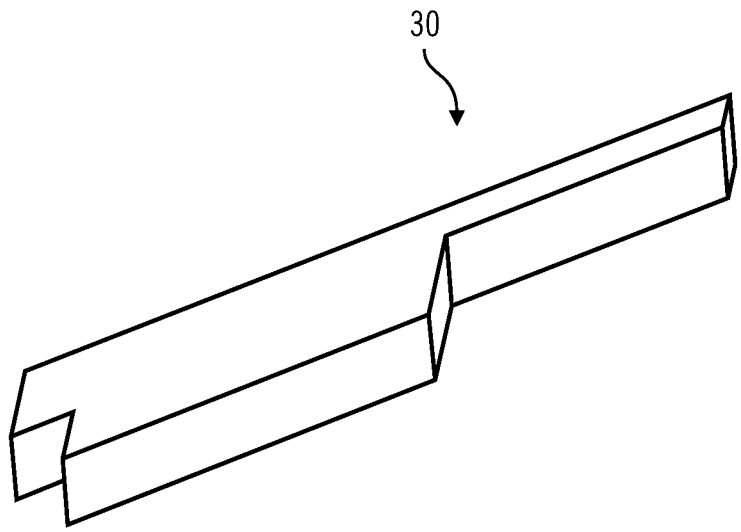
FIG. 3 is a perspective view of an electronics module in accordance with an embodiment of the present invention.

In preferred embodiments, as shown in FIG. 1, an infusion device 10 includes a reservoir 12, a drive system 14, an electronics system 16, a control system 18, and a power supply 20, all contained within a housing 22. The fluid is pushed from the reservoir 12 by the drive system 14 when commanded by the electronics system 16. The power supply 20 provides power to both the drive system 14 and the electronics system 16. A user or another qualified person, such as a doctor, parent, or spouse interfaces with the electronics system 16 through the control system 18. In preferred embodiments, fluid flows from the infusion device 10, through the external tube 24, into an infusion set 26, and then into the individual's body 28, as shown in FIG. 2. Infusion sets 26 that may be used in conjunction with the infusion device 10 are described in, but not limited to, U.S. Pat. Nos. 4,723,947; 4,755,173; 5,176,662; and 5,584,813; and disclosed in U.S. patent application Ser. No. 09/034,626, filed Mar. 4, 1998 and entitled "Medication Infusion Set", which are hereby incorporated by reference.

The control system 18 provides a method for the user or another qualified person to adjust one or more control parameters that the electronics system 16 uses to calculate and issue commands to the drive system 14. Control parameters include, for example, one or more basal rates, one or more bolus rates, maximum and minimum delivery rates, one or more alarm criteria, or the like.

In preferred embodiments, the electronics system 16 is a compilation of one or more electrical elements designed to carryout commands as specified by the control parameters. Electrical elements may include, but are not limited to, resistors, capacitors, amplifiers, diodes, semiconductor circuits, traces, wires, antennae, buttons, sound emanating devices, light emitting devices, receivers, transmitters, switches, or the like. In preferred embodiments, the electrical elements are attached to a single electronics board to form an electronics module. In particular embodiments, an electronics module 30 is a "popsicle stick" design, as shown in FIGS. 3, 5, 10 and 22. The term "popsicle stick" refers to the electronics module's long thin layout that optimizes the usage of space within the housing 22. With the "popsicle stick" design, the electronics module 30 stretches the length of the housing 22 so that only short leads are needed to extend from the electronics module 30 to any component that uses electricity or signals from the electronics. The use of a "popsicle stick" design also facilitates ease of assembly and integrating for the infusion device 10.

Figure 4:
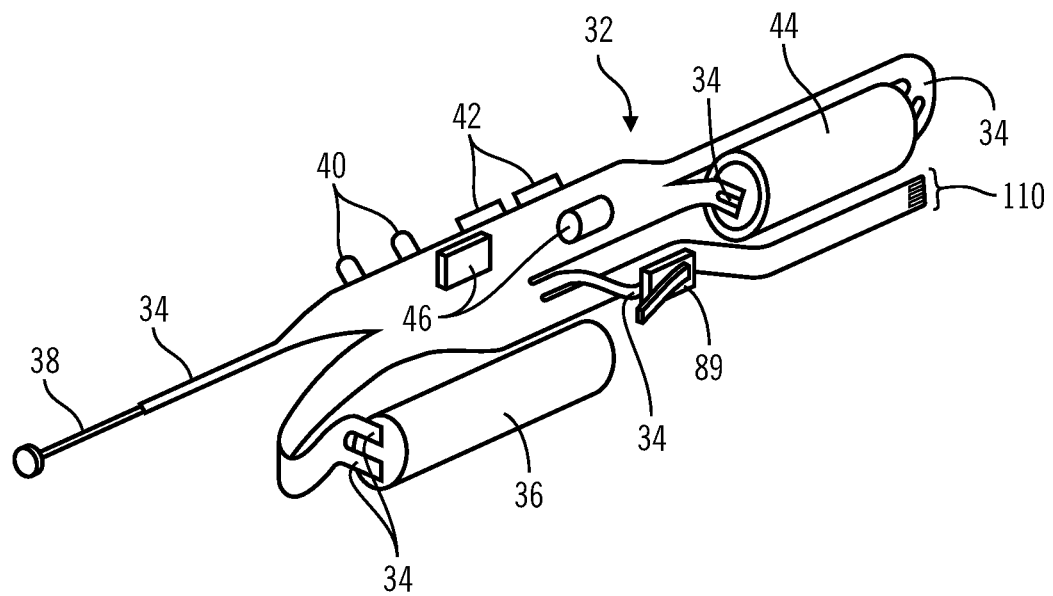
FIG. 4 is a perspective view of a flex circuit in accordance with an embodiment of the present invention.

In alternative embodiments, the electrical elements of the electronics module are mounted on a flex circuit. Preferably, the flex circuit has one or more flex circuit leads 34 that run to various locations within the housing 22 to minimize or eliminate the need for wires. An example of one embodiment of a flex circuit 32 is shown in FIG. 4. Flex circuit leads 34 may run to a motor 36, an antenna 38, one or more LEDs 40, one or more buttons 42, a battery 44, electrical elements 46, or the like. In additional embodiments, the flex circuit 32 may connect to other devices or components such as a transmitter, a receiver, a display, an alarm, a tab, a communication port, a power port, or the like. In additional embodiments, one or more semiconductor circuits are wire bonded to the flex circuit 32.

In preferred embodiments, the electronics module 30 includes chip-on-board construction. In alternative embodiments, the electronics module 30 includes ball grid array (BGA) packages or leaded chip construction.

In preferred embodiments, the electronics system 16 includes one or more LEDs 40 to indicate specific conditions about the infusion device 10, such as whether the fluid is being dispensed, the battery power level, the fluid level in the reservoir 12, whether the electronics system 16 is functioning, warnings regarding how soon the infusion device 10 will require servicing, or the like. In preferred embodiments, the electronics system 16 includes one or more alarms. Preferably, an alarm is a piezo electric sound device. In alternative embodiments, the one or more alarms includes a vibrator, a light, a sound emanating device, or the like.

Figure 5:
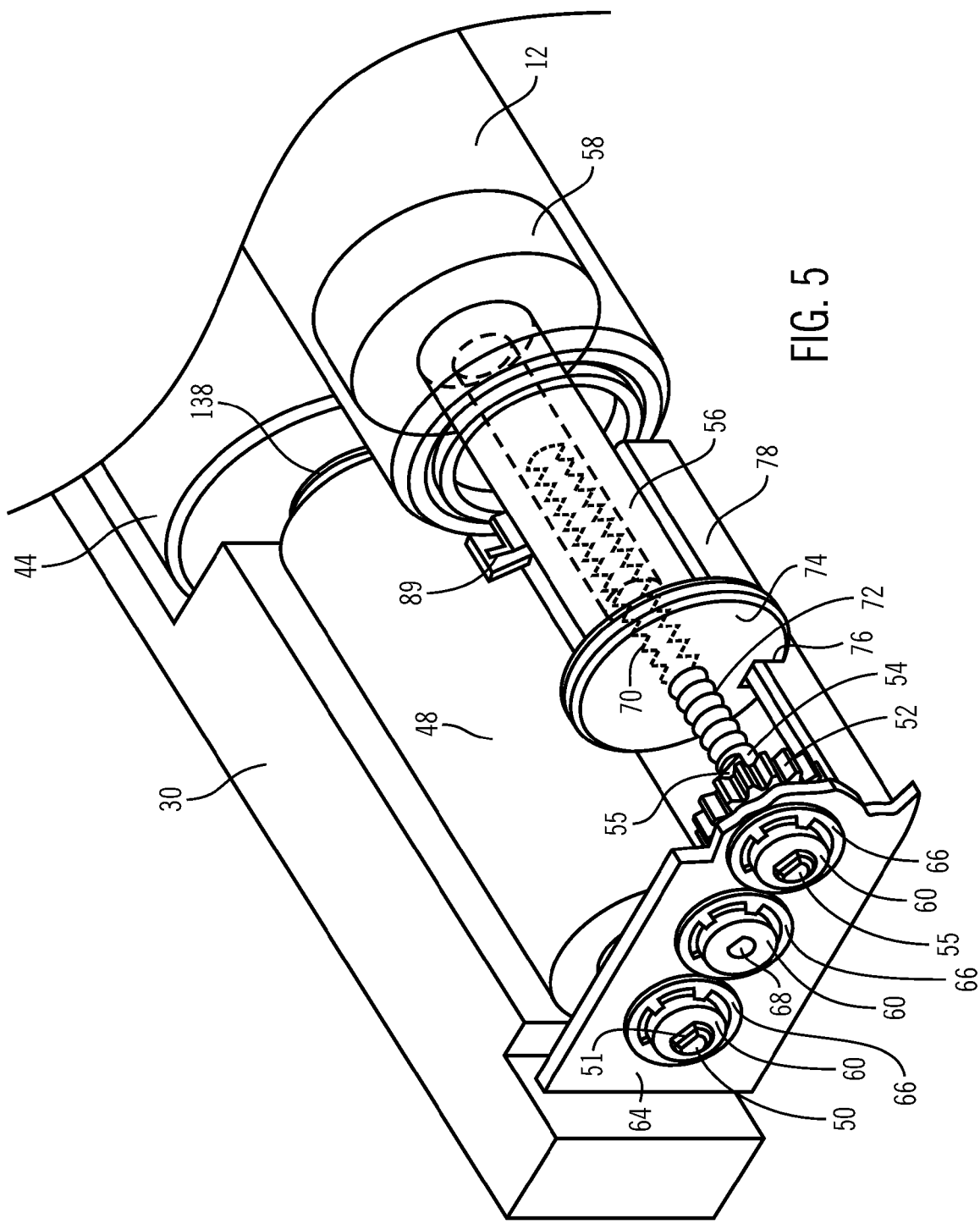
FIG. 5 is a partial perspective view of an infusion device drive system in accordance with an embodiment of the present invention.
Figure 22:
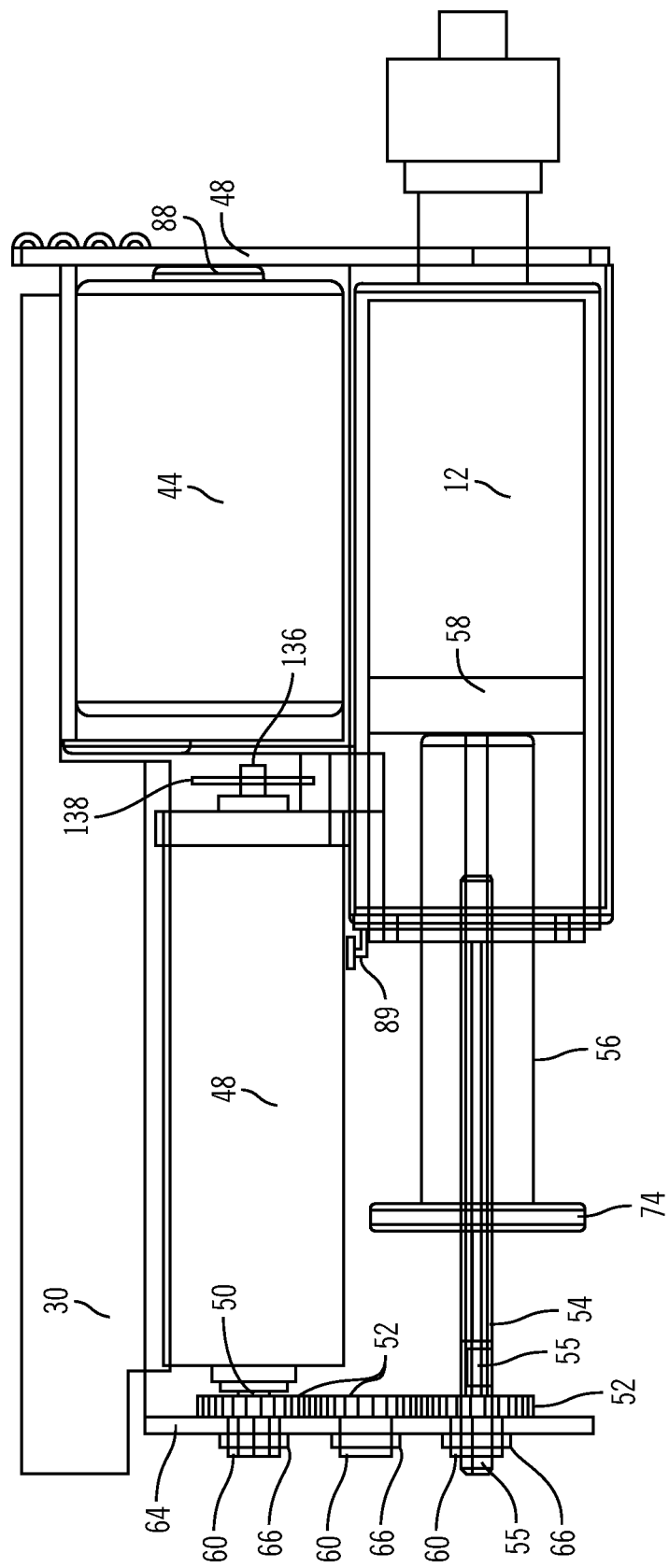
FIG. 22 is a plan view of the internal components of an infusion pump in accordance with an embodiment of the present invention.
Figure 23:
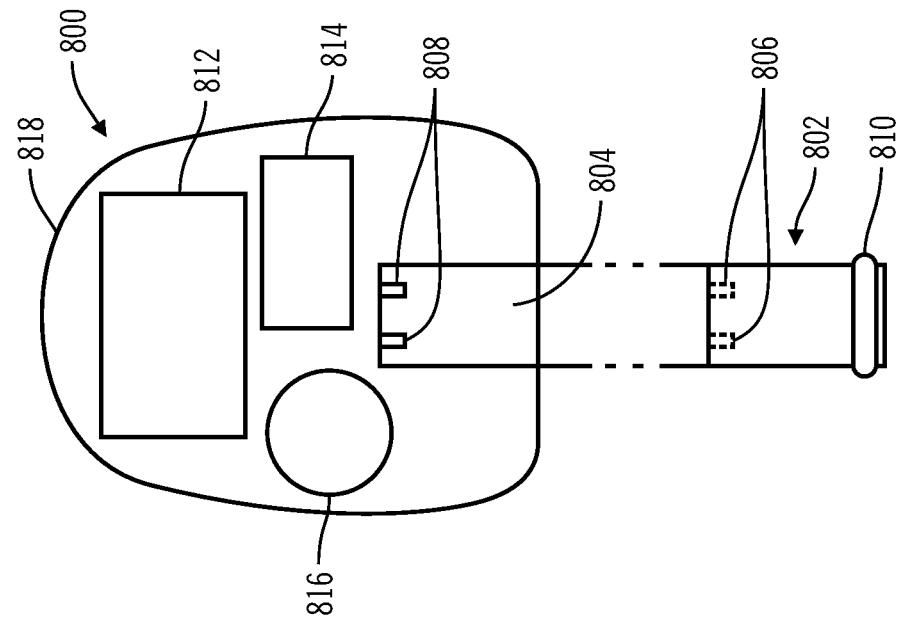
FIG. 23($a$) is a partial cutout perspective view of an infusion device with a tab in accordance with an embodiment of the present invention.
Figure 23:
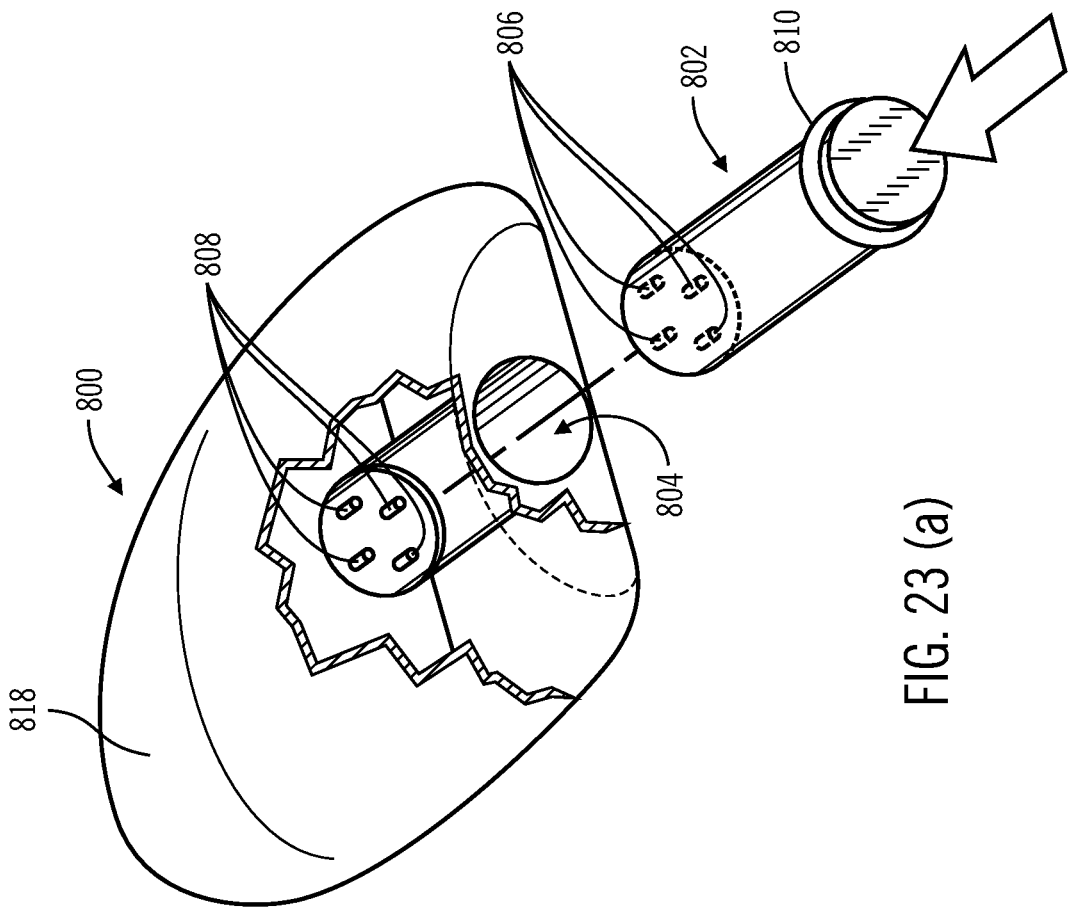

In preferred embodiments, as shown in FIGS. 5 and 22, the drive system 14 includes a motor/gear box 48 with a drive shaft 50 that extends out of the motor/gear box 48, one or more gears 52 external to the motor/gear box 48 that transfers motion from the drive shaft 50 to a lead screw 54, and a piston 56 that is coupled to the lead screw 54, such that as the lead screw 54 rotates, the piston 56 moves a plunger 58 inside the reservoir 12. The angular rotation of a motor shaft 136 is measured with an optical encoder 138 attached to an end of a motor shaft 136 protruding from the motor/gear box 48. In other embodiments, the drive system 14 may also be the same as or similar to the drive mechanism described in, U.S. patent application Ser. No. 09/429,352, filed Oct. 28, 1999 and entitled "Compact Pump Drive System", which is hereby incorporated by reference. In particular embodiments, the motor/gear box 48 includes a stepper motor. In alternative embodiments, the motor/gear box 48 uses a direct current (DC) motor, a solenoid motor or a shape memory alloy (SMA) driven motor. The SMA motor may be of the type described in U.S. patent application Ser. No. 09/249,666, filed on Feb. 12, 1999, entitled "Incremental Motion Pump Mechanisms Powered By Shape Memory Alloy Wire Or The Like", which is hereby incorporated by reference. The SMA motor may include a ratchet/pawl mechanism actuated by a SMA component.

In preferred embodiments, the one or more gears 52 external to the motor/gear box 48 have a one-to-one gear ratio. However, in alternative embodiments, the gears may have different gear rations such as 1.5:1, 2:1, 3:1, 5:1, or the like depending on the motor control resolution and the minimum dosage requirement for the fluid. In particular embodiments, the gears 52 are made of molded plastic. In alternative embodiments, the gears 52 are made of metal, epoxy, laminates, or other suitably strong materials. In alternative embodiments, mechanical power is transferred from the motor/gear box 48 to the lead screw 54 using one or more of a belt, timing belt, chain, gears, rack or the like.

Figure 6:
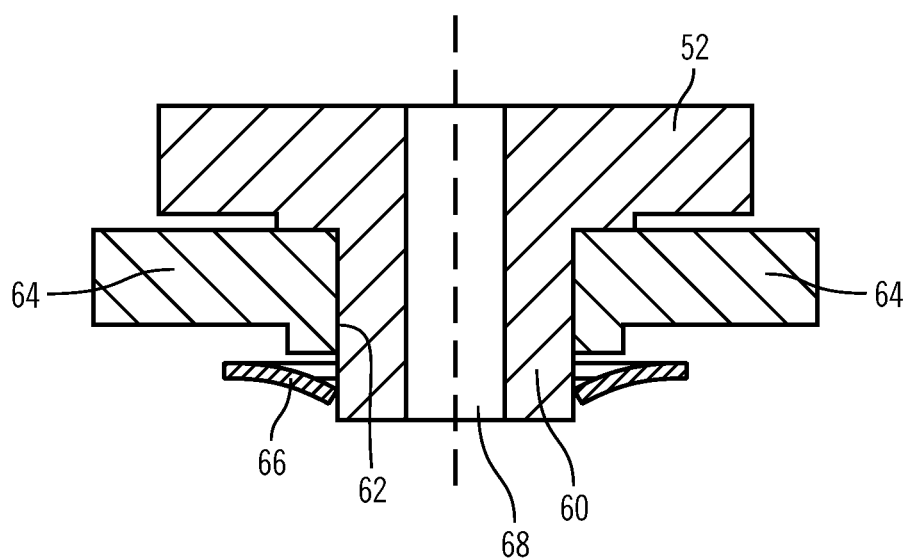
FIG. 6 is a cross-sectional view showing "Tinnerman" style retaining rings holding gear hubs in accordance with an embodiment of the present invention.

As shown on FIG. 6, in preferred embodiments, each of the gears 52 have a gear hub 60 that fits through one of the openings 62 in a wall 64 contained within the housing 22. A "Tinnerman" style retaining ring 66 slips over the gear hub 60 of each gear 52 to secure the gear 52 to the wall 64. In alternative embodiments, each gear hub 60 is held in place with a snap ring, a rivet, a threaded nut, a press-on nut, or the like. In preferred embodiments, each gear 52 has a "D" shaped hole 68 passing entirely through the gear 52 that is located generally at the center of rotation. The drive shaft 50, with a mating "D" shaped end 51, fits into the "D" shaped hole 68 in a gear 52. In addition, a "D" shaped end 55 of the lead screw 54 fits into a "D" shaped hole 68 in a gear 52. The "D" shaped holes 68 function to transmit torque from the drive shaft 50 to the gears 52 and on to the lead screw 54 without the need for a fixed attachment of the drive shaft 50 and the lead screw 54 to the gear hubs 60. In alternative embodiments, other shaped holes are used such as hexagonal, square, rectangular, polygonal, triangular, oval, star, clover, round, notched, or the like along with a drive shaft and a lead screw with mating ends that fit into the holes.

As shown in FIG. 5, in preferred embodiments, the piston 56 has a threaded bore 70 that is generally centered with the piston's longitudinal axis, and the threads 72 on the lead screw 54 mate with the threaded bore 70 on the piston 56. Preferably only the first half of an inch of the piston bore 70 is threaded and the remainder of the bore through the rest of the piston is smooth with a large enough diameter to allow the lead screw to pass through unobstructed. Alternatively, the length of the piston bore that is threaded may be increased or decreased depending on the number of threads needed to apply force to the plunger and the amount of friction generated between the piston bore 70 and the lead screw 54. Preferably, the piston 56 includes a flange 74 with a notch 76 that fits over a rail 78. The rail 78 runs generally parallel to the lead screw 54. As the lead screw 54 rotates, an edge of the notch 76 in the piston flange 74 rests against the rail 78 and prevents the piston 56 from rotating. Therefore, as the lead screw 54 rotates, the piston 56 moves along the length of the lead screw 54 substantially free of rotational movement. In alternative embodiments, the threaded bore 70 in the piston 56 is not generally centered with the piston's centerline. For example, the lead screw 54 may pass through the piston's flange 74.

Figure 7:
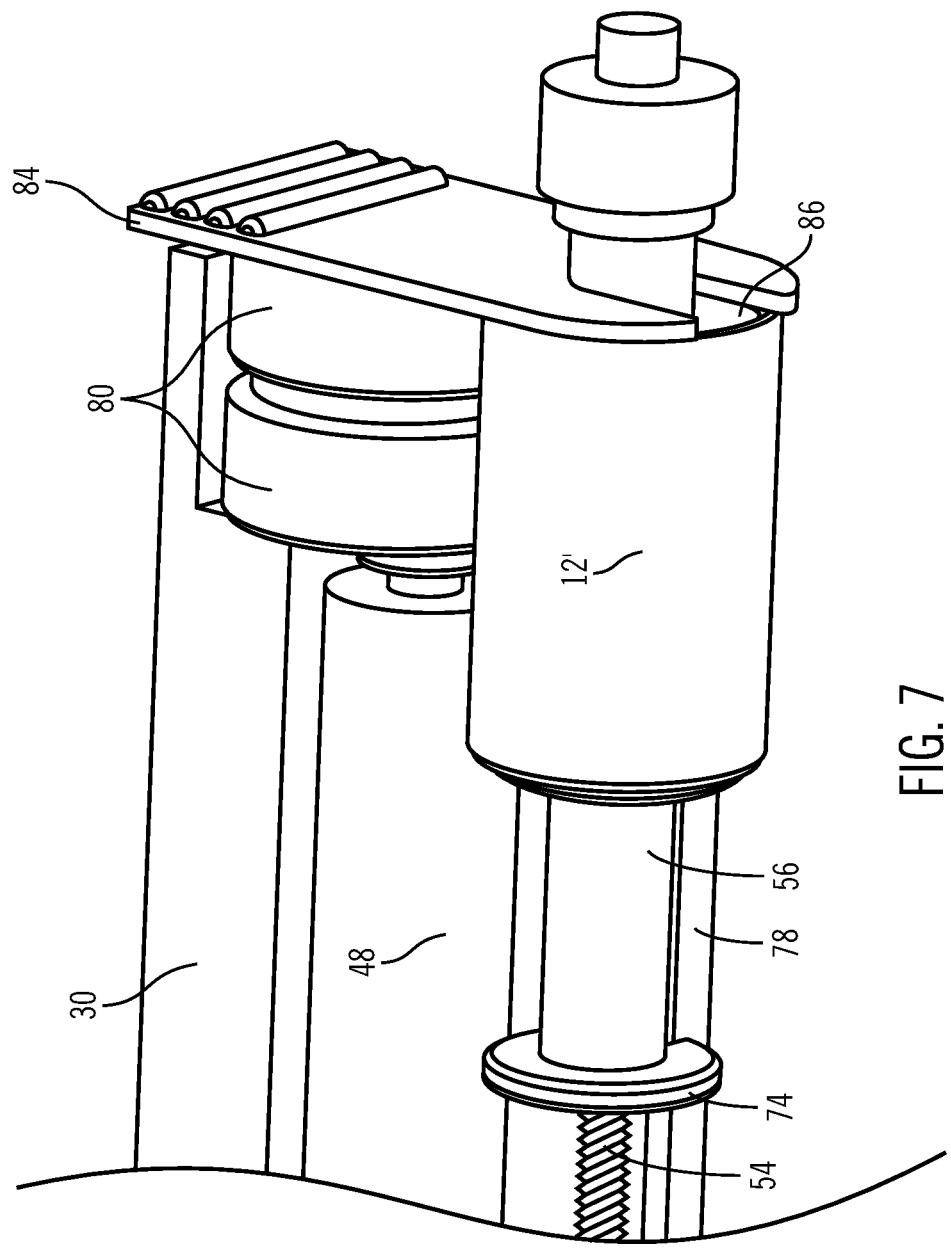
FIG. 7 is a partial perspective view of internal components of an infusion device with multiple batteries in accordance with another embodiment of the present invention.
Figure 10:
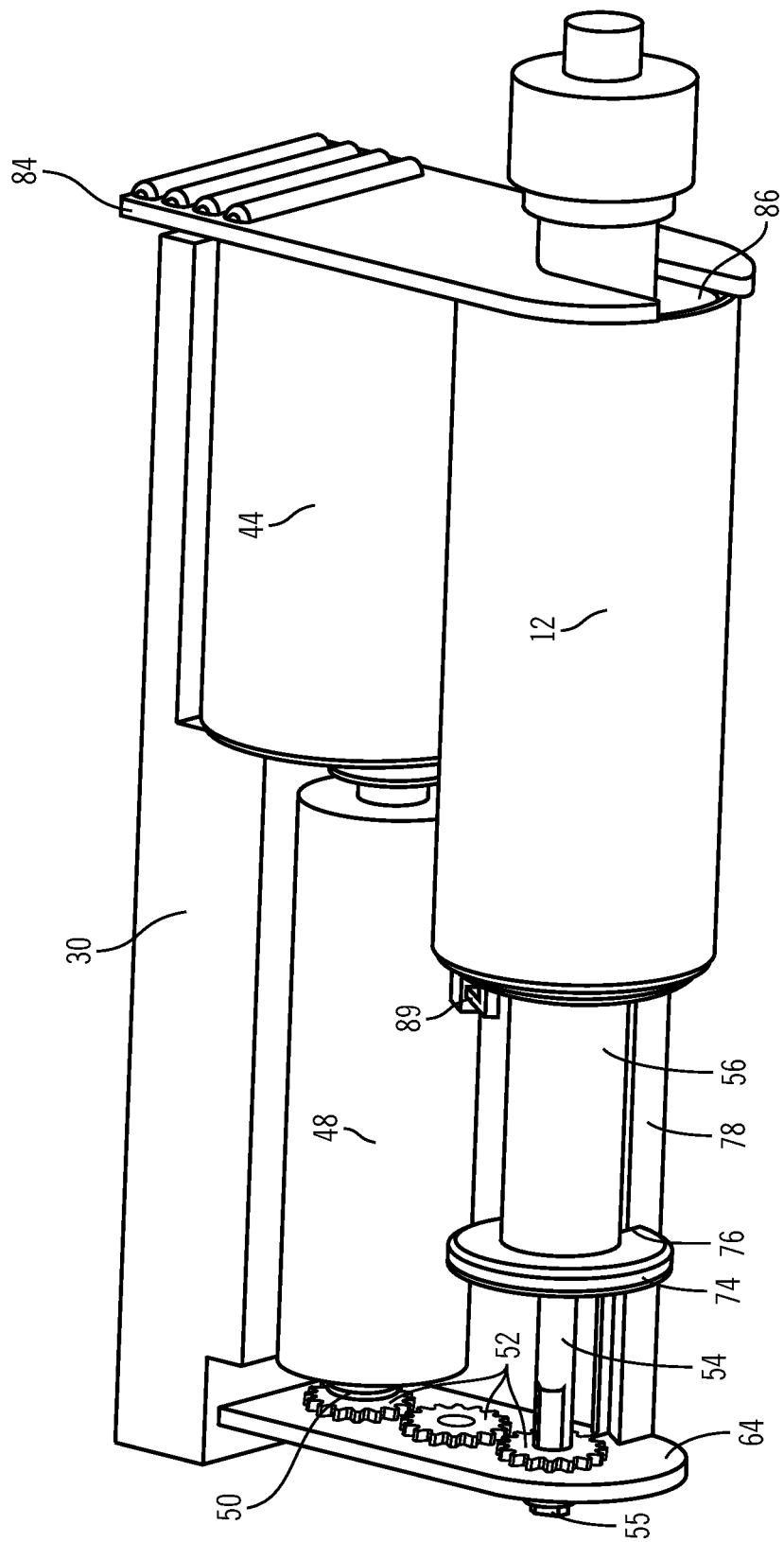
FIG. 10 is a perspective view of the infusion device of FIG. 8 with the housing removed to show the internal components and the key.

In preferred embodiments, the power supply is a battery 44. In particular embodiments, the power supply is a lithium magnesium oxide (LiMnO$_2$) battery 44, as shown in FIGS. 4, 5 and 10. Some of the factors that influence the size of the battery 44 are, the amount of power needed to drive the motor/gear box 48, the amount of friction through out the drive system 14, the size of the reservoir 12 (and therefore the amount of piston 56 displacement needed to empty the reservoir 12), the dosage resolution required, the dosage volume, whether or not alarms are set off, how frequently lights or displays are used, and the number of days desired between battery 44 replacement. In preferred embodiments, the battery 44 lasts at least 10 weeks, while the reusable infusion device 10 dispenses fluid at a rate of up to 40 milliliters per day without alarms. At greater fluid dispensing rates and/or when the alarms are active, the battery duration may be diminished. In preferred embodiments, with a 3 ml reservoir 12, the battery capacity is generally 2.1 amp-hours at 3 volts. In other embodiments, with a 1.5 ml reservoir 12', such as shown in FIG. 7, the combined capacity of a pair of batteries 80, shown in FIG. 7, is generally 1.1 amp-hours at 3 volts. In alternative embodiments, the battery 44 may last as little as 3 days (a common time to empty a reservoir 12) with a battery capacity as low as 0.035 amp-hours. Or, the battery 44 may last as long as a year (a likely time to have the infusion device 10 serviced) with a better battery capacity as large as 12.6 amp-hours. And in other alternative embodiments, the battery voltage may be as low as 0.5 volts and as large as 9 volts depending on the power needed for the drive system 14 and electronics system 16. In further alternative embodiments, two or more batteries (FIG. 7) may be used to supply the voltage and capacity needed to operate the infusion device 10.

Figure 8:
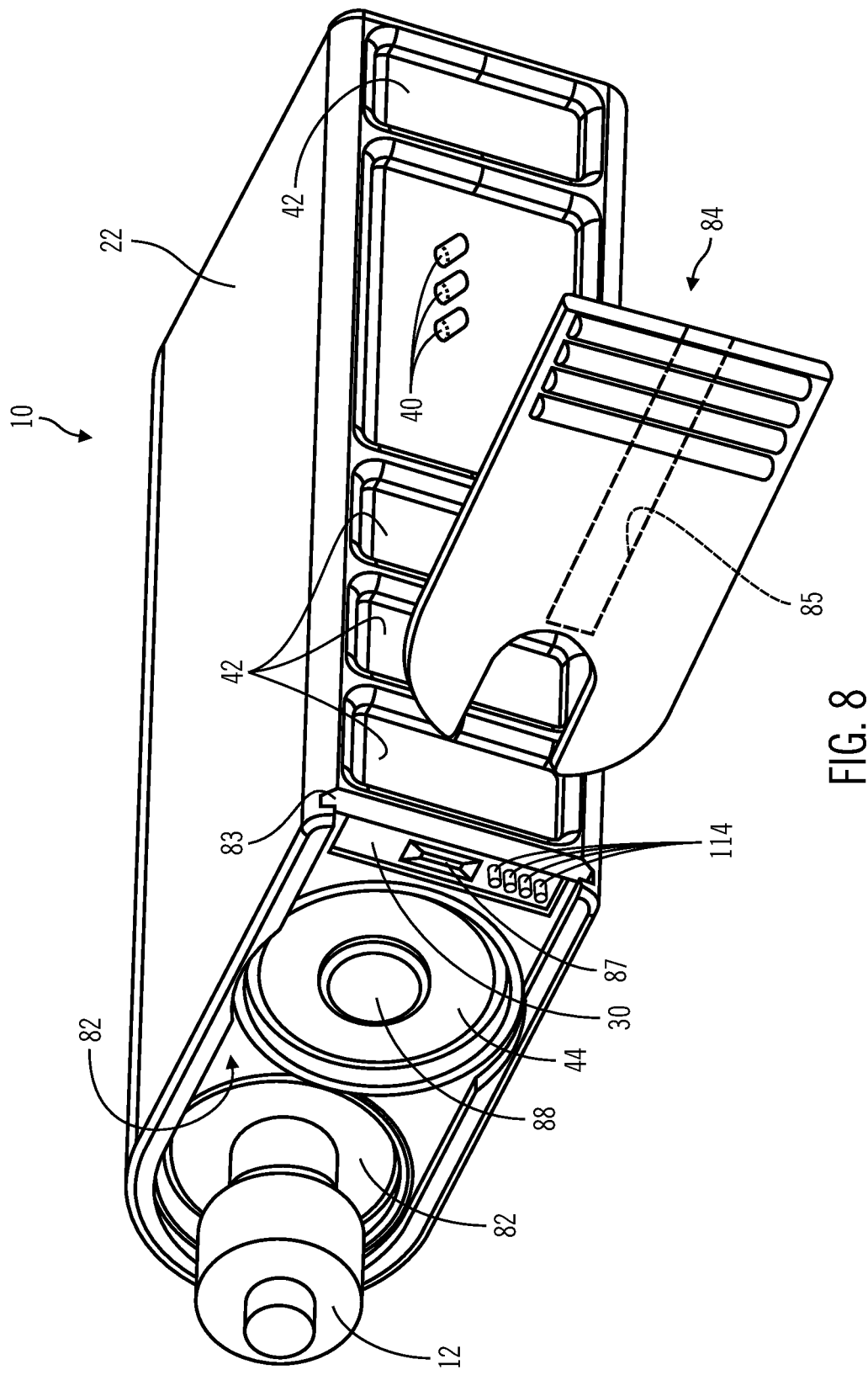
FIG. 8 is a perspective view of an infusion device with a key slid out of the housing in accordance with an embodiment of the present invention.

In preferred embodiments, the battery 44 and reservoir 12 are removable through an opening 82 in the housing 22, and the opening 82 may be closed by sliding a key 84 into a slot 83 formed in the housing 22 so that the key 84 covers the battery 44 and slides over the shoulder 86 of the reservoir 12, as shown in FIGS. 8, and 10. In this embodiment, the key 84 may be slid part way out of the slot 83 of the housing 22 to a detent position that provides a sufficient opening to remove the reservoir 12 from the housing 22 while retaining the battery 44 in place within the housing 22. The battery 44 and the reservoir 12 may both be removed from the housing 22 by entirely removing the key 84 from the slot 83 to fully expose the opening 82. In alternative embodiments, two different sliding keys (not shown) are used, one to slide over the battery 44 and another to slide over the shoulder 86 of the reservoir 12.

In preferred embodiments, the key 84 has a conductive trace 85 that connects a battery terminal 88 of the battery 44 to a power lead 87 on the electronics module 30 (see FIG. 8). Alternatively, the entire back of the key 84 could be conductive. Therefore, if the key 84 is removed, battery power is removed from the electronics system 16. In preferred embodiments, a capacitor, or other charge storage device, maintains electrical power for at least 15 seconds and up to 3 minutes after the battery 44 is disconnected from the electronics system 16. This allows an individual time to replace the battery 44 without losing electrically stored information in the electronics system 16. In alternative embodiments, a commonly known DC converter is used to convert AC wall current into the appropriate DC current and a DC jack is plugged into the infusion device 10 to keep the infusion device 10 powered whenever battery power is low or the battery 44 is removed. In additional embodiments, the battery 44 is rechargeable by supplying a DC current to the infusion device 10 such as by plugging in a DC converter. Alternatively, the infusion device 10 may be placed on a cradle to recharge the battery 44 using induction, solar cells, or use other methods of supplying current to a battery. In additional alternatives the infusion device 10 may be powered directly using solar cells, a DC power supply such as an exterior battery or a DC converter plugged into an AC outlet, and the like.

In preferred embodiments, a switch 89 (shown in FIGS. 4, 5 and 10) is located in the housing 22 so that when the reservoir 12 is inserted far enough into the housing 22, an end of the reservoir 12 contacts the switch 89 causing the switch 89 to toggle. The switch 89 is also spring loaded to return to its original position when the reservoir 12 is removed. Thus, the switch 89 detects when the reservoir 12 is removed from the housing 22. In alternative embodiments, the infusion device 10 may include an optical reader that optically detects when a reservoir is present. In preferred embodiments, when the reservoir 12 is removed from the housing 22, the motor/gear box 48 is automatically triggered to run in reverse to fully retract the piston 56 in preparation for a new reservoir 12 to be installed. In alternative embodiments, the motor/gear box 48 retracts the piston 56 when the key 84 is removed far enough to permit removal of the reservoir 12.

In preferred embodiments, the infusion device 10 is disabled by the electronics system 16 when a predetermined usage life is expired. For instance, the electronics system 16 keeps track of the number of times the reservoir 12 is replaced and compares that number to a specified number that is programmed into a software program in the electronics system 16. Thus, the electronics system 16 will shut down the infusion device 10, stopping the flow of fluid, after the reservoir 12 is replaced a specified number of times. In preferred embodiments, the predetermined life of the infusion device 10 is expired when the reservoir 12 has been replaced sixty times. In alternative embodiments, the number of times that the reservoir 12 may be replaced before the predetermined life of the infusion device 10 is expired may be as many as one hundred and fifty times or as few as twenty times due to the durability of the components that might wear, how carefully individuals handle the infusion device 10, the types of climates the infusion device 10 is subjected to, or the like. In additional alternative embodiments, other measurements are used to detect when the infusion device's predetermined life is expired such as, the number of days of use, the number of times the battery 44 is replaced, an increase in the amount of battery power consumed to empty a reservoir 12, the number of times a key 84 is removed from the infusion device 10, or the like.

In preferred embodiments, the infusion device 10 may be refurbished and returned to the user to be used again after the electronics system 16 has disabled the infusion device 10 due to exceeding its predetermined life. In particular embodiments, the infusion device 10 can be refurbished at least once before its total life is expired. In particular embodiments, the predetermined life may increase or decrease after refurbishing due to a change in the quality of a replacement part, a new lubrication method, new information about the durability of the infusion device 10, how well the user cares for the particular infusion device, or the like. In alternative embodiments, the infusion device 10 is not refurbishable. In other alternative embodiments, the infusion device 10 may be refurbished at least 2 times and up to an indefinite number of times before its total life is expired and it can no longer be used. In particular embodiments, measurements are taken to determine if the total life of the infusion device 10 has expired such as, a significant physical shock detected by an accelerometer (perhaps a shock greater than 2.5 gs, depending on the amount of shock the infusion device 10 can handle), an increase in the amount of battery power consumed to empty a reservoir 12, a maximum temperature such as 120 degrees F. has been exceeded, the reservoir has been replaced too many times (such as 1,000 times), or the like.

In preferred embodiments, the electronics system 16 stores the control parameters, and default control parameters are programmed into the electronics system 16 during manufacturing. Preferably, the control parameters may be changed by an individual using the control system 18. In preferred embodiments, the control system 18 of the infusion device 10 has buttons 42 accessible through the housing 22. In particular embodiments, a button 42 is used to command a bolus. In other particular embodiments, additional buttons 42 may provide additional control features such as to undo a previous command, confirm a command, activate a function, initialize a software program, initialize a new reservoir 12, reset one or more control parameters to a default value, modify a control parameter, withdraw the piston 56, or the like. In preferred embodiments, LEDs indicate that control parameters have been modified by turning on or off, flashing, changing color, sequencing, or the like. In alternative embodiments, the electronics system includes a LCD, LED display, or other displays to show the status of control parameters and/or indicate to the user, which control parameters, are being modified. In other alternative embodiments, other feedback methods such as sounds, vibrations, or the like are used to indicate the status of control parameters.

In other embodiments, a supplemental device 90 is used as, or is used in addition to, the control system 18 to adjust, change, modify, program, input, or the like, one or all of the control parameters. The supplemental device 90 interfaces with the electronics system 16 as shown in FIG. 1. Preferably, the supplemental device 90 includes a display 98, an input system 100 and a communication system 102 that interfaces with the infusion device 10. The communication system 102 provides an initiating signal to the infusion device 10 to cause the control system 18 to go into a programming mode. Alternatively, no initiating signal is needed. Preferably the communication system 102 provides 2-way communication between the supplemental device 90 and the infusion device 10, as shown in FIG. 1. Alternatively the communication system 102 may be one way.

Figure 9:
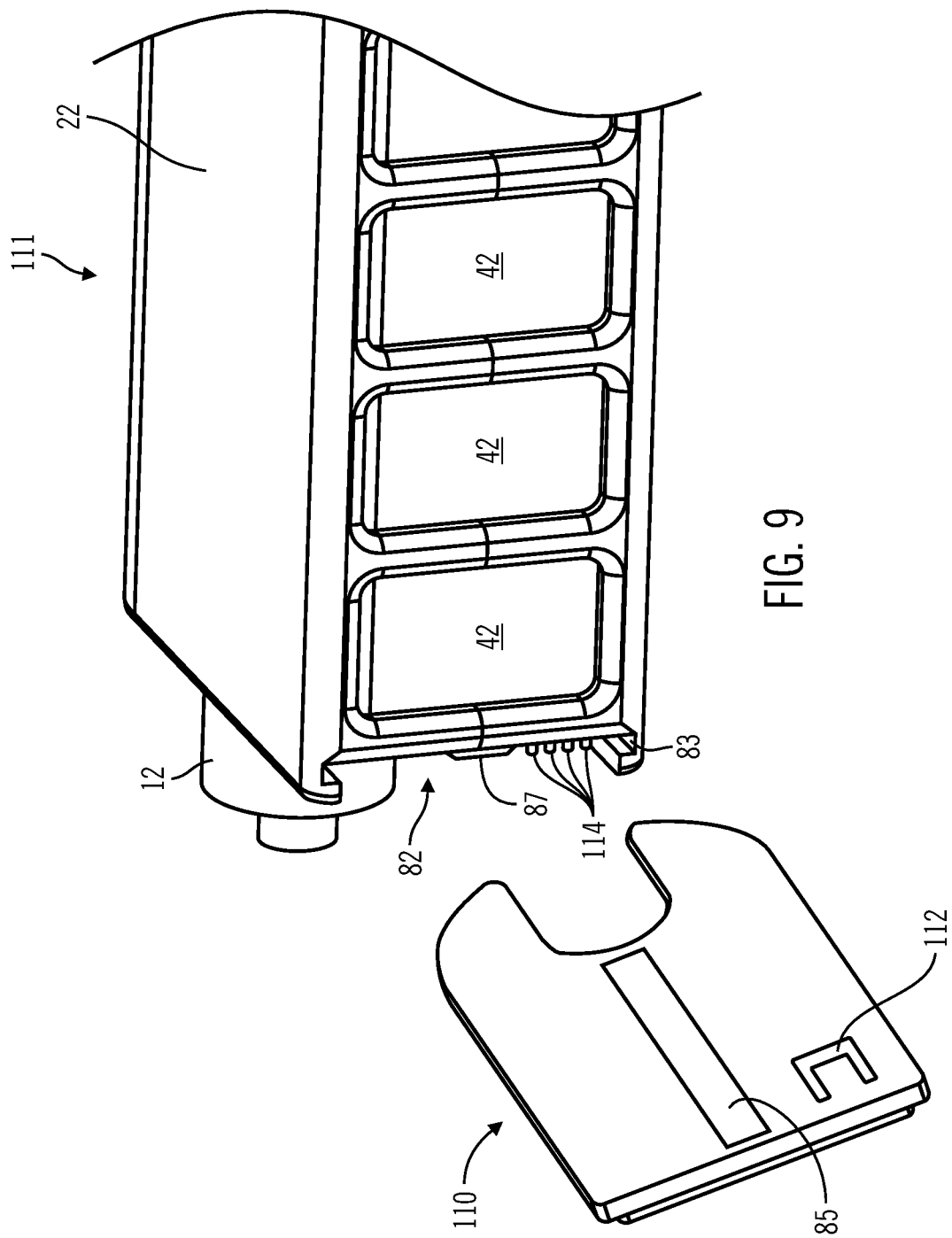
FIG. 9 is a partial perspective view of an infusion device with a key that has electrical traces in accordance with another embodiment of the present invention.
Figure 11:
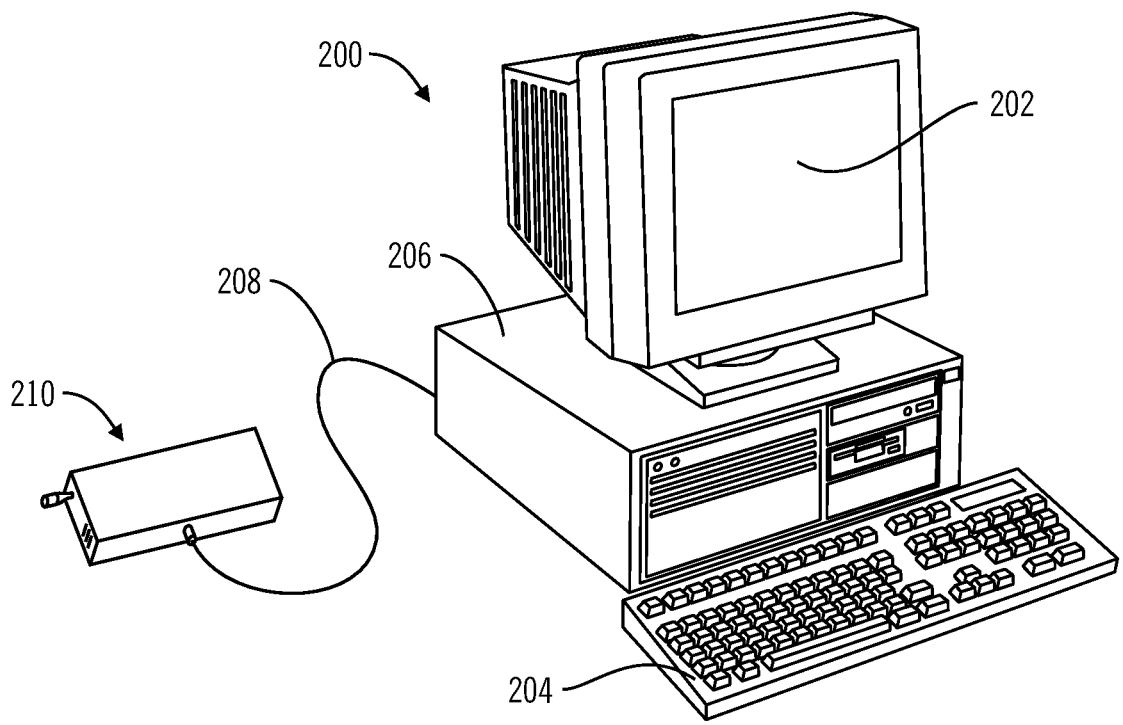
FIG. 11 is a perspective diagram of an infusion device connected to a computer in accordance with an embodiment of the present invention.
Figure 12:
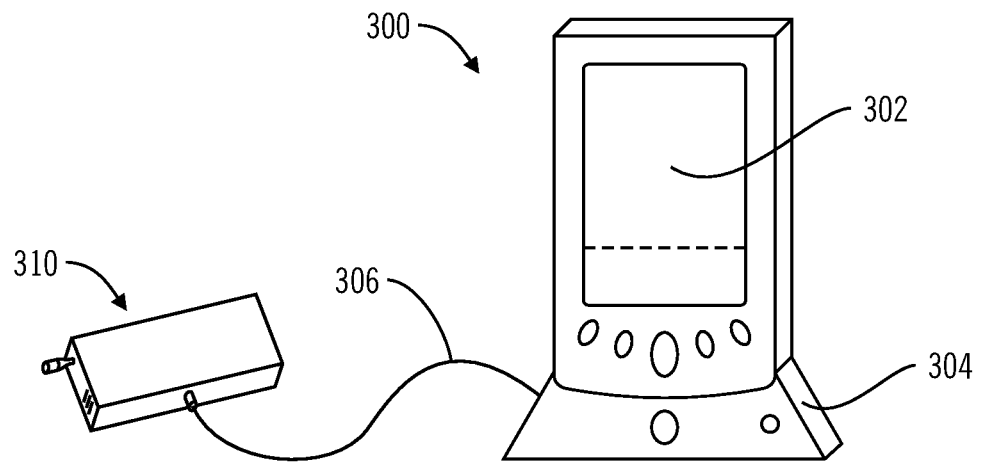
FIG. 12 is a perspective diagram of an infusion device connected to a personal digital assistant in accordance with an embodiment of the present invention.
Figure 13:
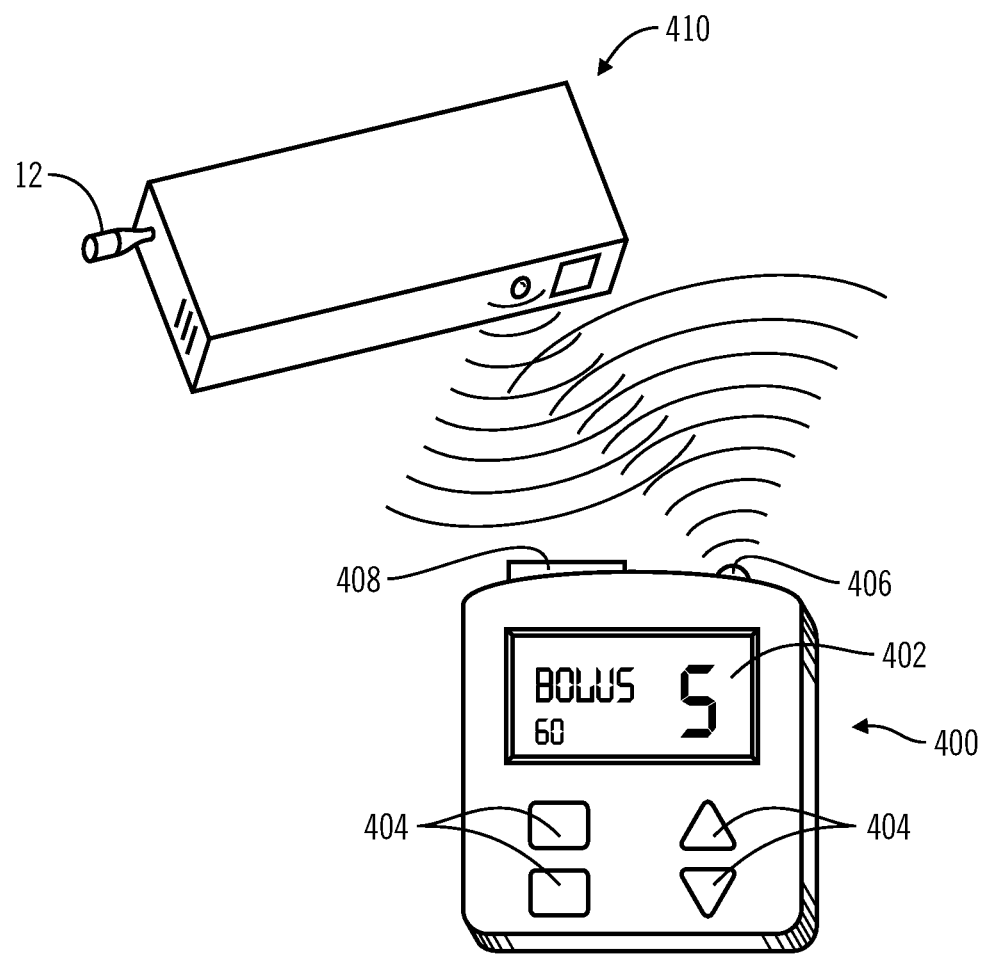
FIG. 13 is a perspective diagram of an infusion device communicating with a dedicated programming device in accordance with an embodiment of the present invention.
Figure 19:
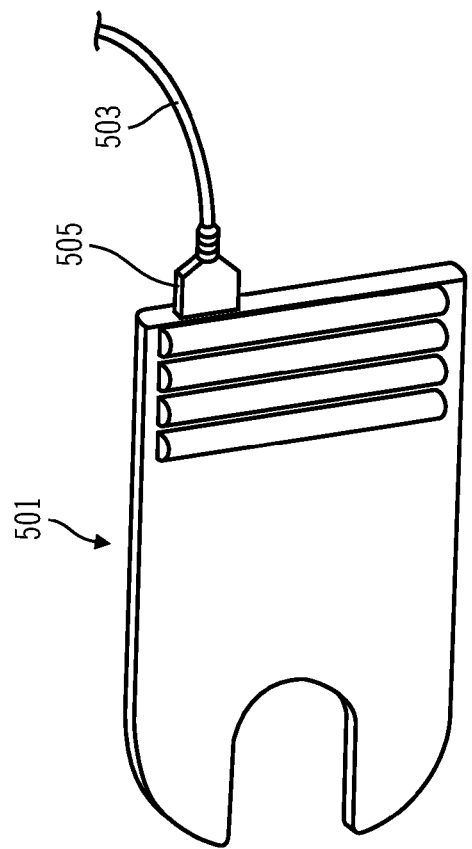
FIG. 19($a$) is a perspective view of a communication key with a slot to accept a connector in accordance with an embodiment of the present invention.

In particular embodiments, the supplemental device 90 is a computer system 200 that communicates with an infusion device 210. The computer system 200 has a monitor 202 as the display, a keyboard 204 as the input system, and the computer 206 and wires 208 as the communication system, as shown in FIG. 11. In preferred embodiments, the wires 208 are detachable at the infusion device 210. In alternative embodiments, the wires 503 carry information between the supplemental device 90 to a communication key 501, shown in FIGS. 19(a) and 19(b). The wires 503 connect to the communication key 501 through a connector 505 that mates with slot 507 in the key 501. The communication key 501 carries the information signals through electrical traces (not shown) to electrical terminals 114 on the infusion device, such as shown in FIG. 9. In particular embodiments, the wires 503 are detachable from the communication key 501 as shown in FIGS. 19(a) and 19(b). In other embodiments, the wires 503 do not detach from the communication key. In further embodiments, the supplemental device 90 is a personal digital assistant (PDA) 300 or a hand held computer such as a Palm Pilot that communicates with an infusion device 310. The PDA 300 has a touch screen LCD 302 that performs the duties of both the display and the input system, while the cradle 304 and wire 306 serve as the communication system, as shown in FIG. 12. In still further embodiments, the PDA may communicate using a wireless connection, such as by IR, RF, or the like. In still other embodiments, the supplemental device 90 is a dedicated programming device 400, that communicates with an infusion device 410 as shown in FIG. 13. The dedicated programming device 400 has a LCD 402 for its display, buttons 404 as the input system and a radio transmitter 406 and receiver 408 as the communication system.

In alternative embodiments, the communication system 102 in the supplemental device 90 uses IR signals, optical signals, direct electrical contact, laser signals, combinations of carrier frequencies, or the like. In further alternative embodiments, the display 98 is monitor, a touch screen, LEDs, lights, or the like. In more alternative embodiments, the input system 100 includes a keyboard, a button, a touch screen, a touch pad, a dial, a switch, a microphone, a joystick, a computer mouse, a roller ball, or the like.

Figure 21:
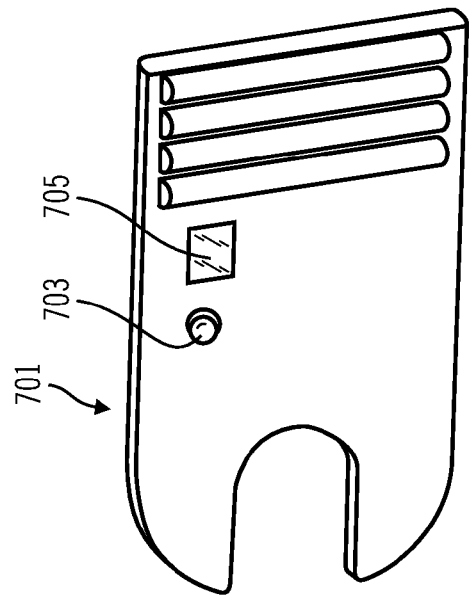
FIG. 21 is a perspective view of a communication key for IR communication in accordance with an embodiment of the present invention.
Figure 19:
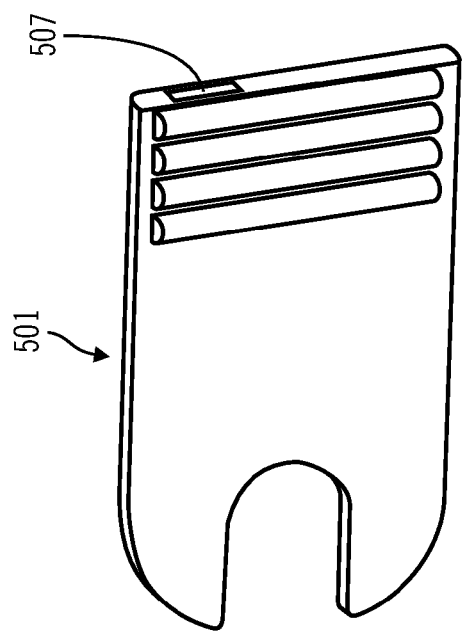
Figure 20:
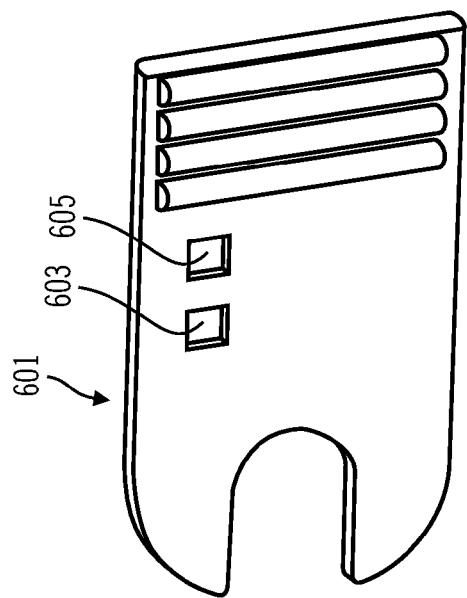
FIG. 20 is a perspective view of a communication key for RF communication in accordance with an embodiment of the present invention.

In particular alternative embodiments, a communication key is used that includes portions of the communication system. For example, a communication key 601 has a radio frequency transmitter 603 and receiver 605, shown in FIG. 20. Alternatively, a communication key 701 has a infra red transmitter 703 and receiver 705, shown in FIG. 21. Other communication devices may be included in the communication key that use other carriers such as, ultrasonic, visual light, video frequencies, ultra violet, laser, microwave, or the like. In alternative embodiments, installation of the communication key into the infusion device causes the control system of the infusion device to go into a programming mode. In particular alternative embodiments, the infusion device enters a programming mode when the communication key contacts a switch (not shown), contacts electrical terminals 114, is detected by a sensor such as an optical or magnetic proximity sensor, pushes a button, or the like.

Figure 14:
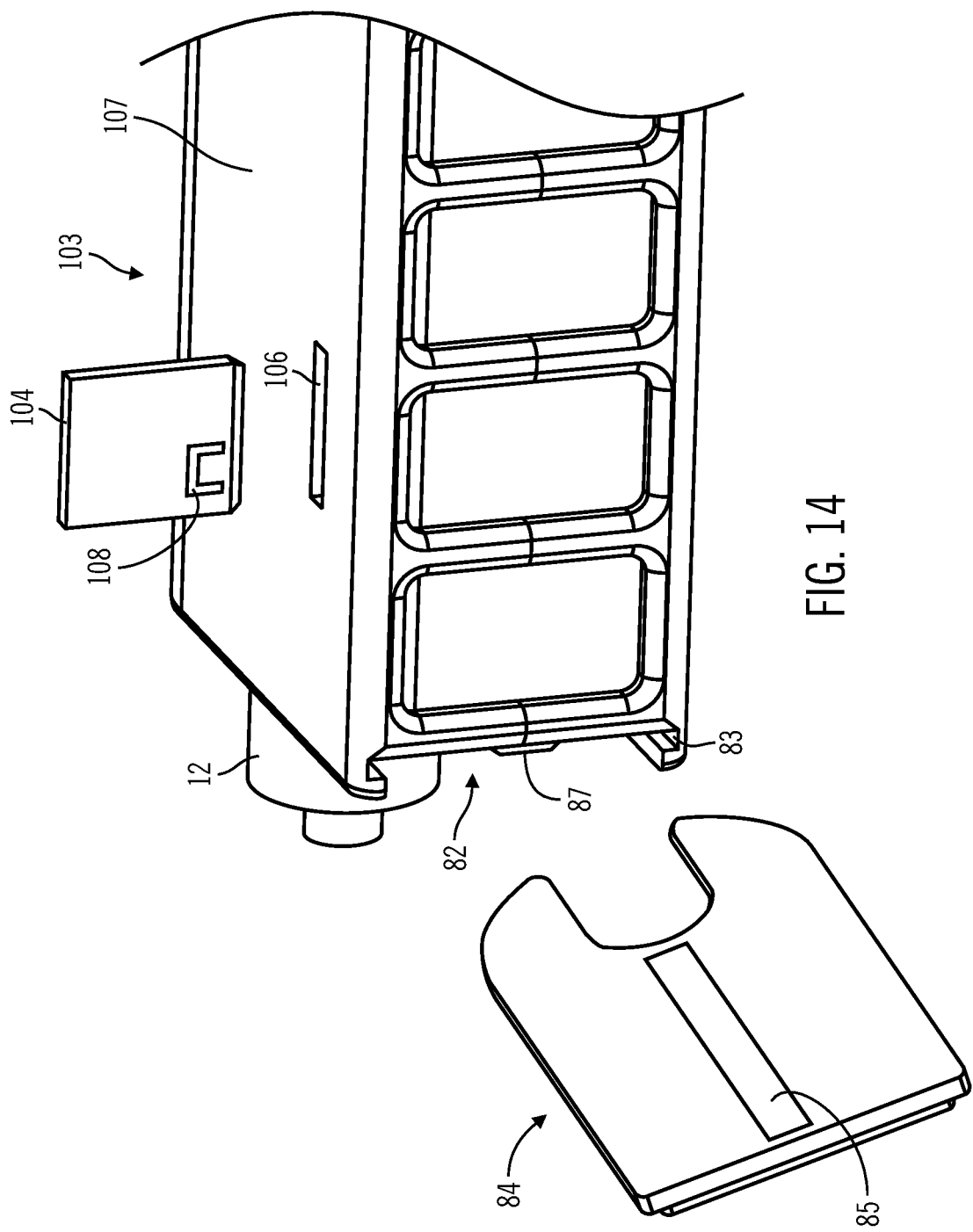
FIG. 14 is a partial perspective view of an infusion device with a tab that has electrical traces in accordance with a further embodiment of the present invention.
Figure 15:
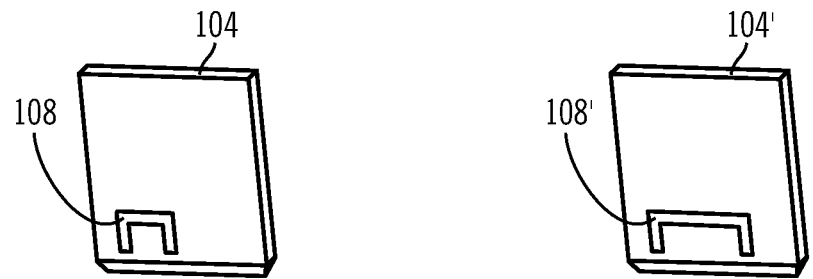
FIG. 15 is a perspective view of two tabs with different electrical traces in accordance with an embodiment of the present invention.

In another embodiment, control parameters such as the basal and/or bolus levels, maximum or minimum basal rate or the like, are set in an infusion device 103 when a tab 104, with at least one conductive trace 108, is inserted into a slot 106 on the housing 107, such as shown in FIG. 14. The conductive trace 108 establishes connections between some of the electrical terminals (not shown) in the infusion device 103. Different patterns of conductive traces 108 and 108' on different tabs 104 and 104' (shown as examples in FIG. 15) connect different electrical terminals (not shown) in the infusion device 103. As different electric terminals (not shown) are connected to each other, different control parameters, such as basal rates, are set and then used by the electronics system 16. The number of electrical terminals (not shown) and the number of conductive traces 108 may vary depending on the number of control parameters that are controlled using the tabs 104. The number of different patterns of unique conductive traces 108, and therefore different tabs 104, is dependent on the number of control parameters that are controlled with the tabs 104 and the number of variations needed for each command parameter. As an example of an application using tabs 104 to control the infusion device 103, a doctor may prescribe a particular basal rate and therefore insert a particular tab 104 into the infusion device 103. Later, if a patient's needs have changed, the doctor may remove the originally prescribed tab 104 and insert a different tab 104 that causes the infusion device 103 to dispense the fluid at a different rate. In alternative embodiments, the tabs may include an optical pattern that is read by an optical reader in the housing. For instance, the optical pattern may be similar to that shown in FIG. 15. Alternatively, other patterns or a bar codes may be used. In further alternative embodiments, the tabs may include information stored on a magnetic media. And the information may be read by a magnetic reader contained within the housing.

Figure 16:
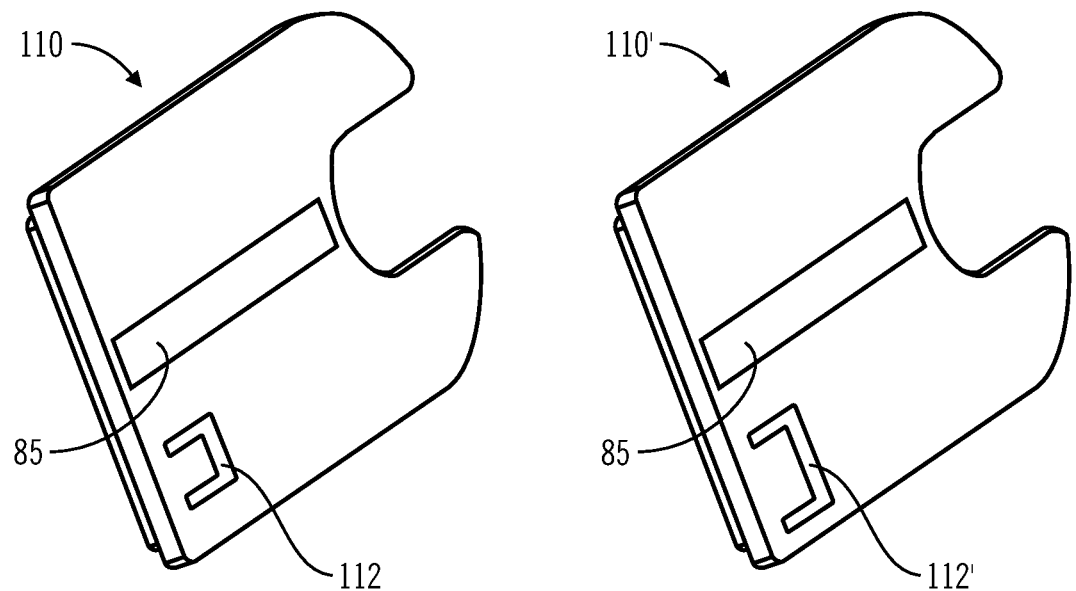
FIG. 16 is a perspective view of two keys with different electrical traces in accordance with an embodiment of the present invention.

In alternative embodiments, the tab is in the form of a tab/key 110 that slides into slot 83 on an infusion device 111 to hold the battery 44 and/or reservoir 12 in place as shown in FIG. 9. Conductive traces 112 on the tab/key 110 establish connections between some of electrical terminals 114. Different patterns of conductive traces 112 and 112' on different tab/keys 110 and 110' (shown as examples in FIG. 16) connect different electrical terminals 114. Again, as different electrical terminals 114 are connected to each other, different control parameters such as basal rates, or the like, are set and used by the electronics system 16.

Figure 17:
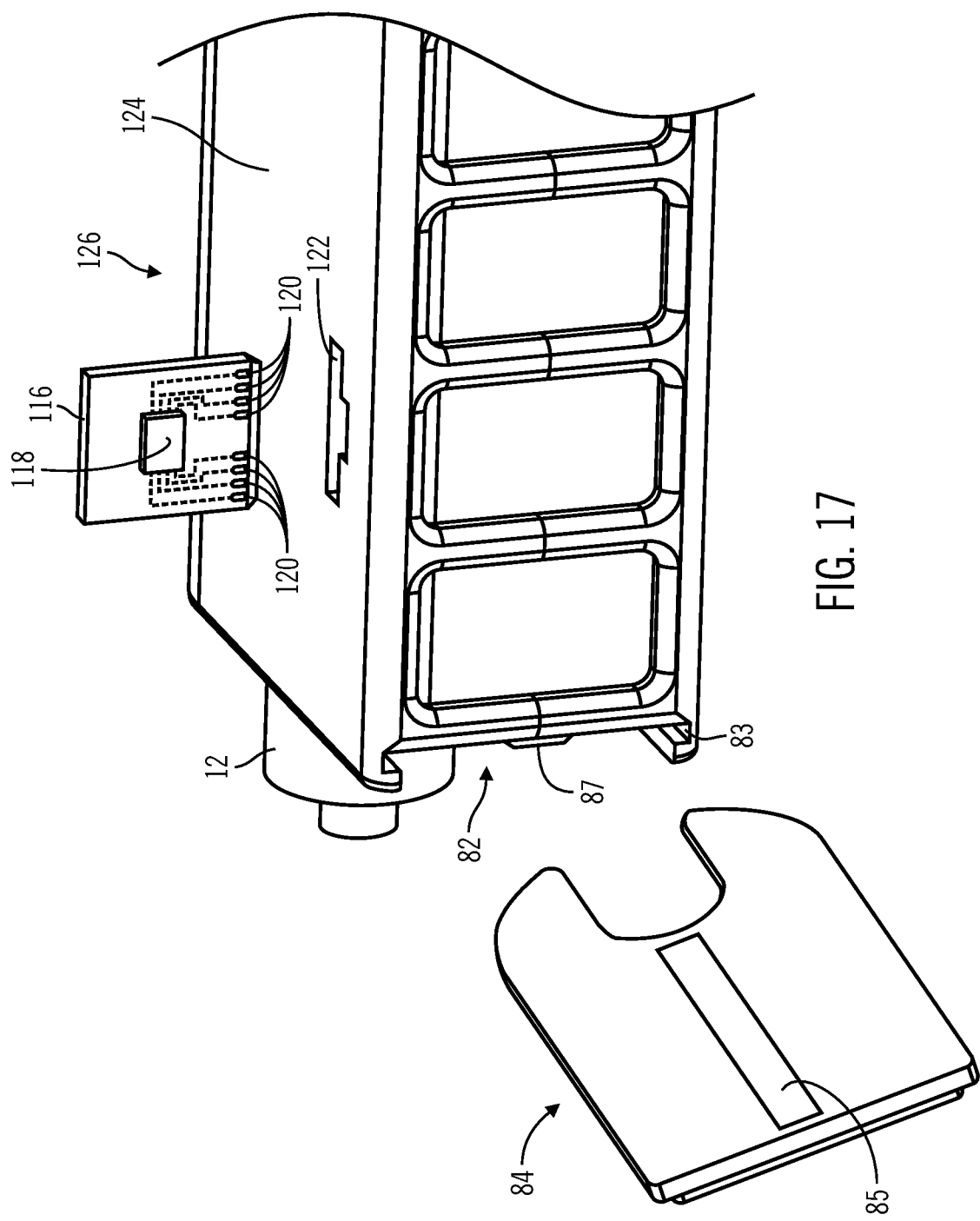
FIG. 17 is a partial perspective view of an infusion device with a tab that has a programmable chip in accordance with an embodiment of the present invention.

In other embodiments, a tab 116 has a programmable chip 118, such as shown in FIG. 17, which is programmed with different control parameters before insertion into a slot 122 in a housing 124 of an infusion device 126. One or more conductive traces 120 on the tab 116 connect the chip 118 to the electronics system 16 through electrical terminals (not shown) in the housing 124. In particular embodiments, different tabs 116 have chips 118 that are programmed with different basal rates. Therefore, to change the basal rate for an infusion device 10, an individual may remove the existing tab 116 from the housing 124 and install a different tab 116 that includes a chip 118 that is programmed to command a different basal rate. In particular embodiments, the tabs 116 are removed from the infusion device 126, and the chips 118 are re-programmed with different control parameters, and then the tab 116 is re-installed into the infusion device 126. In alternative embodiments, the chips 118 are not re-programmable, and a new tab 116 with a new chip 118 is used when control parameters must be changed.

Figure 18:
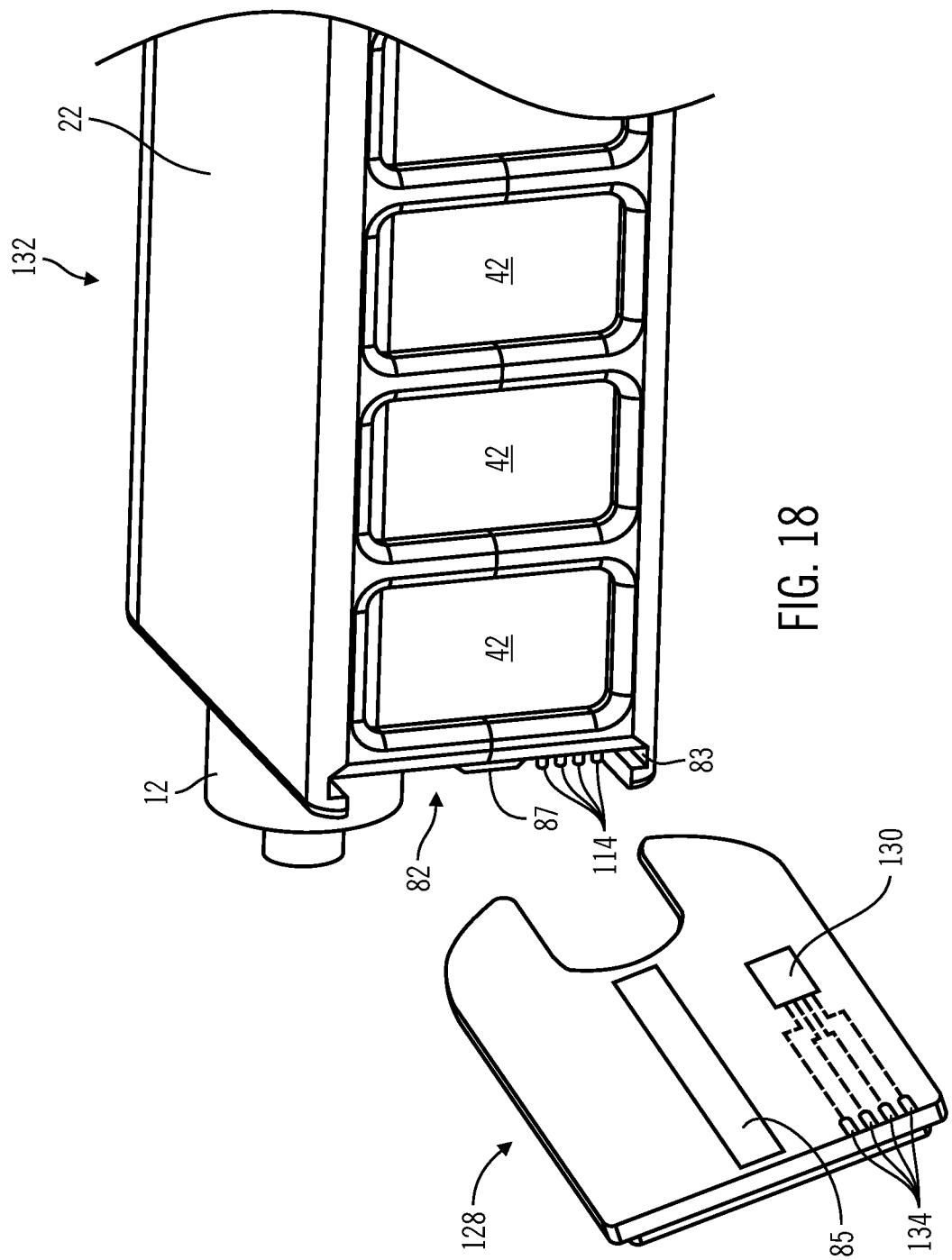
FIG. 18 is a partial perspective view of an infusion device with a key that is that has a programmable chip in accordance with an embodiment of the present invention.

In alternative embodiments, the tab is in the form of a tab/key 128 and has a programmable chip 130 such as shown in FIG. 18, which is programmed with different control parameters before insertion into slot 83 of the housing 22 of infusion device 132. One or more conductive traces 134 on the tab/key 128 connect the chip 130 to the electronics system 16 through electrical terminals 114.

In additional alternative embodiments, a tab/key, normally used to establish control parameters as described above, may be a communication key. The communication key enables the infusion device to communicate with a supplemental device 90 to change control parameters or transfer data. In particular embodiments, a tab/key that is not a communication key is reinserted into the infusion device for normal operation after the communication key has completed the communication with the supplemental device 90. In other particular embodiments, the communication key is left in the infusion device or a different tab/key is used after the communication device is removed.

In other particular embodiments, the tab/key includes communication devices. For example, a tab/key with a computer chip (such as tab/key 128 described above) may include a slot to accept a connector such as communication key 501 shown in FIGS. 19(a) and 19(b). Other communication devices such as IR, RF, ultrasonic, or the like may be included on a tab/key. In particular embodiments, the supplemental device 90 can reprogram computer chips included on the tab/key. In alternative embodiments, a communication device is included on a tab that does not serve as the key that covers the battery 44 and the reservoir 12.

In preferred embodiments, the tabs are color coded to identify the basal rate or other control parameters they are programmed to command. In alternative embodiments, other identification methods may be used to indicate the basal rate, and/or other control parameters, associated with a particular tab such as, a code number, a serial number, a lot number, a batch number, a name, or the like. Methods of applying the identification include, stamping, silk-screening, printing, typing, labels, embossing, imprinting, molding, or the like. In additional alternative embodiments, other means are used to identify tabs that have different control parameters from each other such as, surface textures, flexibility, materials, a raised patterns, printed patterns, or the like.

Tabs may be used to modify characteristics of other infusion devices as well, such as those described in U.S. Pat. Nos. 4,562,751; 4,685,903; 5,080,653; 5,505,709; 5,785,688; 5,814,020 and 5,097,122; and disclosed in U.S. patent application Ser. No. 09/334,858, filed Jun. 17, 1999 and entitled "Infusion Pump With Remote Programming and Carbohydrate Calculator Capabilities", and Ser. No. 09/429,352, filed Oct. 28, 1999 and entitled "Compact Pump Drive System", which are hereby incorporated by reference. In particular embodiments, tabs are used in disposable infusion devices, such as shown in FIGS. 23(a)-24(b) and U.S. Pat. Nos. 5,814, 020 and 5,785,688. The infusion device 800, shown in FIGS. 23(a) and (b), has a housing 818, a reservoir 812, a gas generator 814, one or more batteries 816, and a tab 802 that contains one or more electronic elements (not shown). The surface of the housing that abuts or is in contact with the skin may be coated with an adhesive layer for attaching the apparatus to the skin. When the tab 802 is installed into an opening 804 on the infusion device 800, one or more conductive traces 806 come in contact with one or more electrical terminals 808 to provide an electrical contact between the infusion device 800 and the tab 802. A seal 810 closes the opening 804 in the infusion device 800 to prevent contaminants from entering and/or to improve water resistance of the infusion device 800.

In other embodiments, one or more batteries 916 are stored in a tab 902 that mates with an infusion device 900, such as shown in FIGS. 24(a) and (b). The infusion device 900 has a housing 918, a reservoir 912, a gas generator 914, and an opening 904 to receive the tab 902. The tab 902 contains the one or more batteries 906 and one or more electronic elements (not shown). When the tab 902 is inserted into the opening 904 one or more conductive traces 906 come into electrical contact with one or more electrical terminals 908 on the infusion device 900. A seal 910 closes the opening 904 in the infusion device 900 to prevent contaminates from entering and/or to improve water resistance of the infusion device 900.

In still other embodiments, one or more components that are included with the tab are reusable and/or sensitive to sterilization treatments such as, radiation, heat, gas, fog or mist (such as hydrogen peroxide), chemical washes or soaks, and the like. The infusion device without the tab can be processed through a sterilization process before the tab is inserted. Thus, the tab, and any components included with the tab, are excluded from a sterilization process, since these components do not come in contact with fluids or materials infused into the body and do not need to be sterilized.

In some embodiments, the tab may be used in one infusion device, and then removed from the infusion device and installed into another infusion device. For example, a tab may be mated with an infusion device that has been sterilized, and then the infusion device is used for infusing a fluid into an individual. When the infusion device is ready to be replaced due to, for example, a low reservoir, housing damage, or for any other reason, the tab may be removed. Once the tab is removed, the infusion device may be disposed of or re-sterilized. The tab may be reused with a new infusion device or a newly sterilized infusion device, or the tab may be disposed of when no longer useable.

In preferred embodiments, the tab must be inserted into the infusion device for the infusion device to operate. And removal of the tab causes the infusion device to stop fluid delivery. In alternative embodiments, the infusion device continues to operate independent of whether a tab is installed or not.

In preferred embodiments, an LED (light emitting diode) or other indicator may be used on the infusion device or on the tab to indicate that the tab is inserted properly, the drive system is powered, fluid delivery is in process, the power supply status, and the like.

In preferred embodiments, the tab may include, for example, portions of, or all of: an electronics system, drive system, power supply, communication system, output device (such as an LCD, one or more LED's, speaker, sound making device, vibrator, and the like), input devices (such as a key pad, a touch screen, or the like), or the like.

Figure 25:
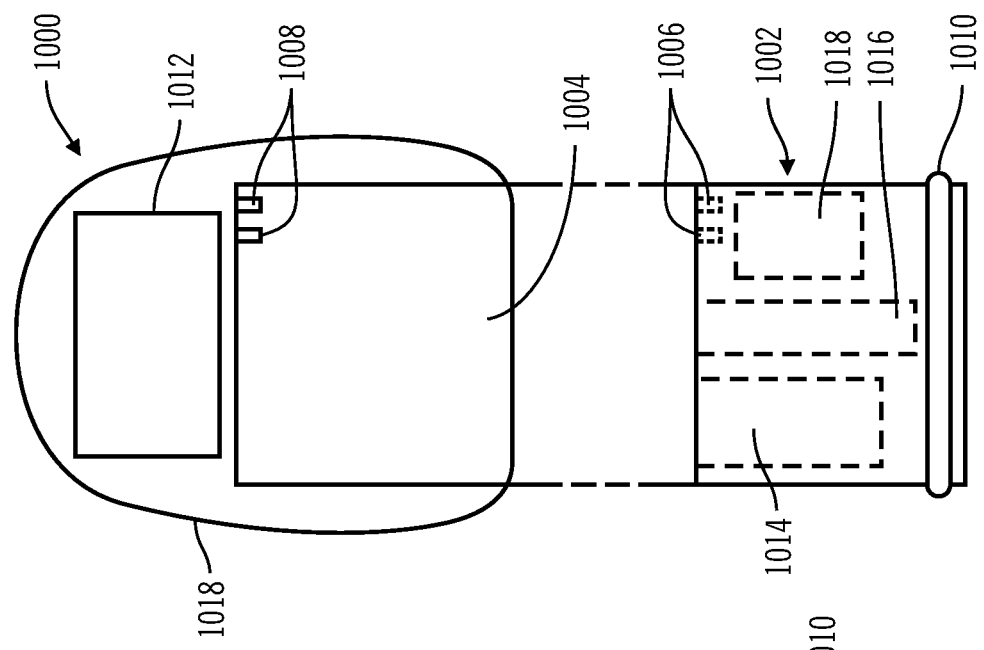
FIG. 25($a$) is a partial cutout perspective view of an infusion device with a tab containing at least one battery, at least one electrical component, and a drive system in accordance with an embodiment of the present invention.
Figure 25:
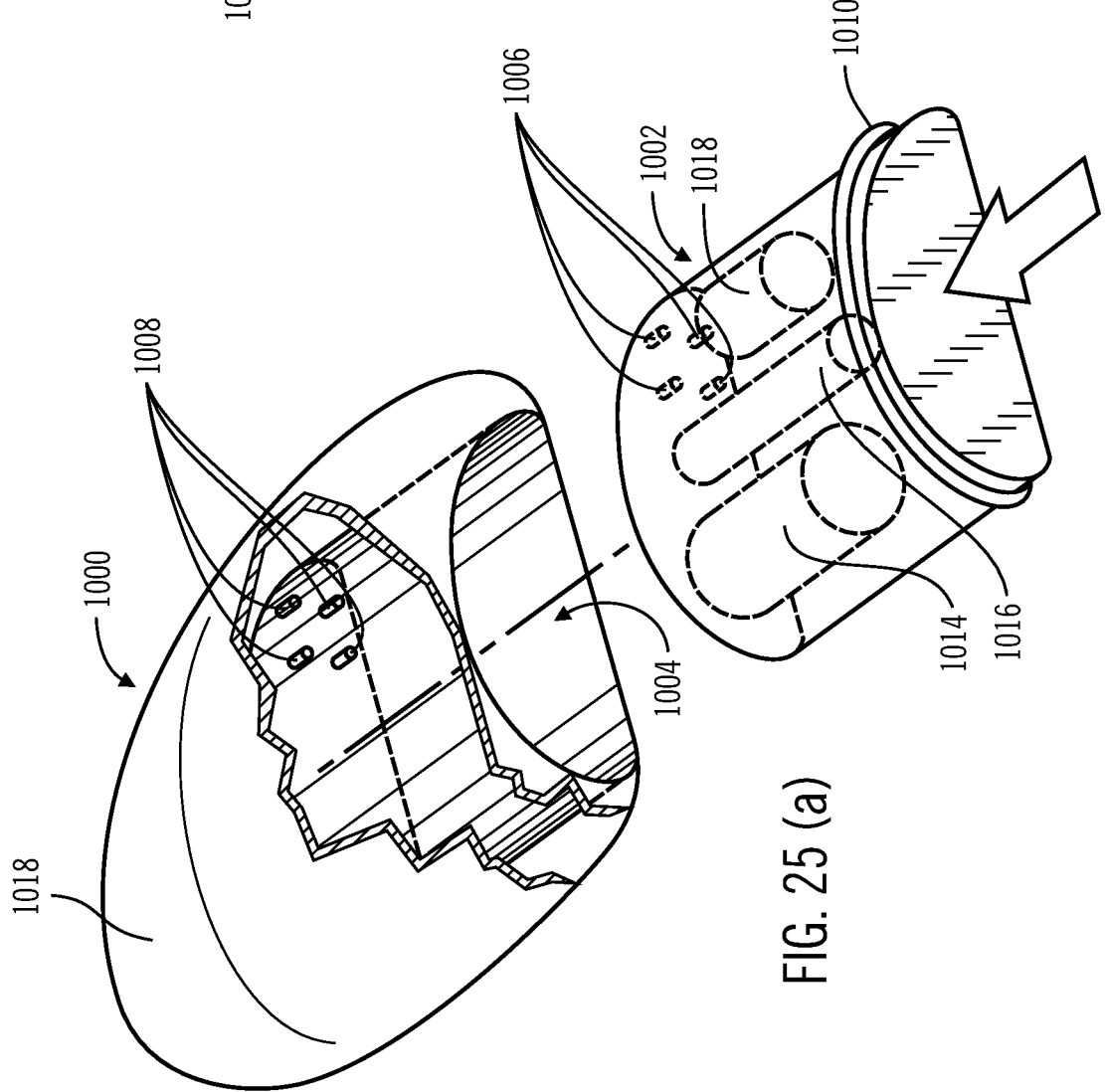

In a particular embodiment, one or more batteries 1016, an electronics system 1018, and a drive system 1014 are included in a tab 1002 that mates with an infusion device 1000, such as shown in FIGS. 25(a) and (b). The infusion device 1000 has a housing 1018, a reservoir 1012, and an opening 1004 to receive the tab 1002. When the tab 1002 is inserted into the opening 1004, one or more conductive traces 1006 come into electrical contact with one or more electrical terminals 1008 on the infusion device 1000. A seal 1010 closes the opening 1004 in the infusion device 1000 to prevent contaminates from entering and/or to improve water resistance of the infusion device 1000. In alternative embodiments, some of the elements 1016, 1018, or 1014 may be omitted entirely.

In alternative embodiments, a tab may be shaped to attach to the external surface of the infusion device. In other embodiments, the tabs may be formed in different shapes and the seals may be omitted, placed in a different position on the tab, or placed on or incorporated in the infusion device.

In some embodiments, the tabs are coded so that tabs with different characteristics (such as electrical elements that cause a different infusion rate, or work with different types of insulin, or add or subtract features, or affect different control parameters) may be identified from one another. For example, the tabs may be different colors, have bar codes or markings, include numbers, letters and/or names, have bumps, be different shapes, have textures or patterns, or the like.

In other embodiments, the tabs may affect the infusion device filling process. In some embodiments, the tab must be installed into the infusion device before the infusion device reservoir is filled with medicament. For instance the tab may activate a valve to open the fluid path, or the tab may include a port for a filling apparatus to mate with the infusion device, of the shape of the tab may limit the shape of the filling apparatus that can be mated with the infusion device to fill the reservoir with medicament, or the like. In these embodiments, different concentrations or different types of medicament may be packaged in different filling apparatuses so that each type of tab will only permit a particular filling apparatus to mate with the infusion device, if the filling apparatus contains medicament that is compatible with the tab. In alternative embodiments, the tab may provide a code or signal to the infusion device indicating which filling apparatuses are compatible with the tab. Alternatively, each filling apparatus may provide a code or signal to the infusion device. If the filling apparatus is not compatible with the tab, the filling apparatus cannot connect with the infusion device and/or the fluid path to the reservoir is not opened to permit filling. Conversely, if the filling apparatus is compatible with the tab, it will connect with the infusion device and the fluid path to the reservoir is opened to permit filling.

In other embodiments, each tab has a limited usage life. In particular embodiments, the tab is removable from the infusion device and may be installed into a different infusion device to affect at least one control parameter of the infusion device. In some embodiments, the tab may only be re-installed into a different infusion device a predetermined number of times, which determines the usage life. Once the usage life is exceeded, the tab will not permit the infusion device to function. In other embodiments, the tab will work for a limited amount of time or until a predetermined amount of medicament is expelled from the infusion device reservoir, or until the reservoir has been emptied a predetermined number of times, or the like.

Tabs may also be used to calibrate or control various features of characteristic or analyte monitor systems such as those described in U.S. patent application Ser. No. 09/465,715, filed Dec. 17, 1999 and entitled "Telemetered Characteristic Monitor System And Method Of Using The Same"; and Ser. No. 09/246,661, filed Feb. 5, 1999 and entitled "An Analyte Sensor And Holter-Type Monitor System And Method Of Using The Same"; and also Ser. No. 09/334,996, filed Jun. 17, 1999 and entitled "Characteristic Monitor With A Characteristic Meter And Method Of Using The Same", which are all hereby incorporated by reference herein.

In preferred embodiments, substantially all parts of the infusion device 10 are designed to slide or snap together during assembly. In particular embodiments, no screws are used on the infusion device 10. In preferred embodiments, the housing 22 is plastic and is sealed using ultrasonic fusing. In alternative embodiments, other methods are used to seal the housing 22 such as gluing, bonding, fusing, melting, snapping, pressing, or the like. In other alternative embodiments, the housing 22 is made of other materials such as metal, rubber, resin, foam, or the like. Refurbishing of the infusion pump 10 may require destruction of the housing 22.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An infusion system for infusing a fluid into a body, comprising:
   an infusion device having
      a first surface having an adhesive layer for attaching the infusion device to the skin, and
      a second surface having one or more electrical terminals;
   a replaceable fluid containing reservoir;
   a needle or cannula in communication with the reservoir and extending through a periphery the first surface of the infusion device; and
   a tab that removably mates with the second surface of the infusion device to form and seal a housing when mated with the infusion device, the tab having
      a drive system to force the fluid from the reservoir,
      an electronics system to control the drive system,
      one or more batteries to power the electronics system and the drive system, and
      one or more conductive traces;
   wherein one or more components included with the tab are reusable, and wherein the one or more conductive traces come in contact with the one or more electrical terminals when the tab mates with the second surface to provide an electrical contact between the infusion device and tab.

2. The infusion system of claim 1, wherein the tab further includes at least one of a communications system, an output device, and an input device.

3. The infusion system of claim 1, wherein the one or more components included with the tab are sensitive to sterilization treatments.

4. The infusion system of claim 1, wherein the reservoir can only be filled once.

5. The infusion system of claim 1, wherein the infusion device or the tab further includes an indicator to indicate at least one of the drive system is powered, fluid delivery is in process, and power supply status.

6. An infusion system for infusing a fluid into a body, comprising:
   an infusion device having
      a first surface having an adhesive layer for attaching the infusion device to the skin, and
      a second surface having one or more electrical terminals;
   a replaceable fluid containing reservoir;
   a needle or cannula in communication with the reservoir and extending through a periphery of the first surface of the infusion device; and
   a tab that removably mates with the second surface of the infusion device to form and seal a housing when mated with the infusion device, the tab having
      at least a portion of a drive system to force the fluid from the reservoir,
      an electronics system to control the drive system,
      one or more batteries to power the electronics system and the drive system, and
      one or more conductive traces;
   wherein one or more components included with the tab are reusable, and wherein the one or more conductive traces come in contact with the one or more electrical terminals when the tab mates with the second surface to provide an electrical contact between the infusion device and tab.

7. The infusion system of claim 6, wherein the tab further includes at least one of a communications system, an output device, and an input device.

8. The infusion system of claim 6, wherein the one or more components included with the tab are sensitive to sterilization treatments.

9. The infusion system of claim 6, wherein the reservoir can only be filled once.

10. The infusion system of claim 6, wherein the infusion device or the tab further includes an indicator to indicate at least one of the drive system is powered, fluid delivery is in process, and power supply status.

11. An infusion system for infusing a fluid into a body, comprising:
    an infusion device having
       a first surface having an adhesive layer for attaching the infusion device to the skin, and
       a second surface having one or more electrical terminals;
    a replaceable fluid containing reservoir, the reservoir can only be filled once;
    a needle or cannula in communication with the reservoir and extending through a periphery of the first surface of the infusion device; and
    a tab that removably mates with the second surface of the infusion device to form and seal a housing when mated with the infusion device, the tab having
       at least a portion of a drive system to force the fluid from the reservoir,
       an electronics system to control the drive system,
       one or more batteries to power the electronics system and the drive system, and
       one or more conductive traces;
    wherein one or more components included with the tab are reusable, and wherein the one or more conductive traces come in contact with the one or more electrical terminals when the tab mates with the second surface to provide an electrical contact between the infusion device and tab.

12. The infusion system of claim 11, wherein the tab further includes at least one of a communications system, an output device, and an input device.

13. The infusion system of claim 11, wherein the one or more components included with the tab are sensitive to sterilization treatments.

14. The infusion system of claim 11, wherein the infusion device or the tab further includes an indicator to indicate at least one of the drive system is powered, fluid delivery is in process, and power supply status.

15. The infusion system of claim 1, wherein the tab has a predetermined usage life that is programmed into the electronics system, and when the predetermined usage life for the tab expires, the electronics system disables the tab from infusing the fluid from the reservoir into the body; and
    wherein the predetermined usage life for the tab is programmed into the electronics system as a predetermined amount of time that the tab is in use.

16. The infusion system of claim 1, wherein the tab has a predetermined usage life that is programmed into the electronics system, and when the predetermined usage life for the tab expires, the electronics system disables the tab from infusing the fluid from the reservoir into the body; and wherein the predetermined usage life for the tab is programmed into the electronics system as a predetermined number of times that the reservoir is emptied.

17. The infusion system of claim 6, wherein the tab has a predetermined usage life that is programmed into the electronics system, and when the predetermined usage life for the tab expires, the electronics system disables the tab from infusing the fluid from the reservoir into the body; and wherein the predetermined usage life for the tab is programmed into the electronics system as a predetermined amount of time that the tab is in use.

18. The infusion system of claim 6, wherein the tab has a predetermined usage life that is programmed into the electronics system, and when the predetermined usage life for the tab expires, the electronics system disables the tab from infusing the fluid from the reservoir into the body; and wherein the predetermined usage life for the tab is programmed into the electronics system as a predetermined number of times that the reservoir is emptied.

19. The infusion system of claim 11, wherein the tab has a predetermined usage life that is programmed into the electronics system, and when the predetermined usage life for the tab expires, the electronics system disables the tab from infusing the fluid from the reservoir into the body; and wherein the predetermined usage life for the tab is programmed into the electronics system as a predetermined amount of time that the tab is in use.

20. The infusion system of claim 11, wherein the tab has a predetermined usage life that is programmed into the electronics system, and when the predetermined usage life for the tab expires, the electronics system disables the tab from infusing the fluid from the reservoir into the body; and wherein the predetermined usage life for the tab is programmed into the electronics system as a predetermined number of times that the reservoir is emptied.

* * * * *